(12) United States Patent
Noda et al.

(10) Patent No.: US 9,387,135 B2
(45) Date of Patent: Jul. 12, 2016

(54) ABSORBENT ARTICLE

(71) Applicant: UNICHARM CORPORATION, Shikokuchuo-shi, Ehime (JP)

(72) Inventors: Yuki Noda, Kanonji (JP); Tatsuya Tamura, Kanonji (JP); Takashi Nomoto, Kanonji (JP); Takashi Onozuka, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 0 days.

(21) Appl. No.: 14/381,952

(22) PCT Filed: Feb. 25, 2013

(86) PCT No.: PCT/JP2013/054796
§ 371 (c)(1),
(2) Date: Aug. 28, 2014

(87) PCT Pub. No.: WO2013/129327
PCT Pub. Date: Sep. 6, 2013

(65) Prior Publication Data
US 2015/0057627 A1 Feb. 26, 2015

(30) Foreign Application Priority Data

Feb. 29, 2012 (JP) .................. 2012-044439
Feb. 29, 2012 (JP) .................. 2012-044524
Feb. 29, 2012 (JP) .................. 2012-044575
Mar. 30, 2012 (JP) .................. 2012-082514

(51) Int. Cl.
*A61F 13/15* (2006.01)
*A61F 13/512* (2006.01)
(Continued)

(52) U.S. Cl.
CPC .......... *A61F 13/5126* (2013.01); *A61F 13/472* (2013.01); *A61F 13/47218* (2013.01);
(Continued)

(58) Field of Classification Search
CPC ............ A61F 13/472; A61F 13/47218; A61F 13/51108; A61F 13/51113; A61F 13/5126; A61F 13/533; A61F 13/51186; A61F 13/5128; A61F 13/512
See application file for complete search history.

(56) References Cited

U.S. PATENT DOCUMENTS 3,929,135 A 12/1975 Thompson
4,588,630 A 5/1986 Shimalla
(Continued)

FOREIGN PATENT DOCUMENTS

CN 1432352 7/2003
EP 1250940 A1 10/2002
(Continued)

OTHER PUBLICATIONS

Atsushi Fujita, "Prediction of Organic Compounds and Organic Conceptual Diagram", Kagaku no Ryoiki (Region of Chemistry), Oct. 1957, p. 719-725, vol. 11, No. 10.
(Continued)

*Primary Examiner* — Bradley Philips
(74) *Attorney, Agent, or Firm* — Hauptman Ham, LLP

(57) ABSTRACT

The present invention addresses the problem of providing a novel absorbent article that prevents excessive compression of an absorbent body caused by deformation of the absorbent article, and rewetting associated with said compression. In order to solve such a problem, a sanitary napkin (1) is provided with a liquid-permeable top sheet (2), a liquid-impermeable back sheet (3), and an absorbent body (4) disposed between the top sheet (2) and the back sheet (3), wherein: an extensible area (21) having an extensible bellows-like section (210), and a flexible area (22) surrounding the extensible area (21) are formed in a waste supply area (20) of the top sheet (2).

10 Claims, 11 Drawing Sheets

(51) Int. Cl.
*A61F 13/472* (2006.01)
*A61F 13/511* (2006.01)
*A61F 13/533* (2006.01)

(52) U.S. Cl.
CPC ..... *A61F13/51108* (2013.01); *A61F 13/51113* (2013.01); *A61F 13/533* (2013.01); *A61F 2013/5128* (2013.01); *A61F 2013/51186* (2013.01)

(56) References Cited

U.S. PATENT DOCUMENTS

| | | | |
|---|---|---|---|
| 4,759,754 | A | 7/1988 | Korpman |
| 5,078,710 | A | 1/1992 | Suda et al. |
| 5,334,176 | A | 8/1994 | Buenger et al. |
| 5,344,416 | A | 9/1994 | Niihara |
| 5,614,283 | A | 3/1997 | Potnis et al. |
| 5,650,214 | A * | 7/1997 | Anderson ............... A61F 13/45 383/118 |
| 5,976,665 | A * | 11/1999 | Hansson ............... A61F 13/512 264/154 |
| 6,153,209 | A | 11/2000 | Vega et al. |
| 6,730,819 | B1 | 5/2004 | Pesce |
| 2001/0029141 | A1 | 10/2001 | Mizutani et al. |
| 2003/0088222 | A1 | 5/2003 | Yoshimasa et al. |
| 2003/0149410 | A1 | 8/2003 | Kudo et al. |
| 2003/0198784 | A1* | 10/2003 | Mizutani ............... A61F 13/511 428/182 |
| 2006/0184150 | A1 | 8/2006 | Noel |
| 2006/0276767 | A1 | 12/2006 | Ueminami et al. |
| 2007/0219515 | A1 | 9/2007 | Marsh et al. |
| 2007/0298213 | A1 | 12/2007 | Noda et al. |
| 2007/0298214 | A1 | 12/2007 | Noda et al. |
| 2007/0298220 | A1 | 12/2007 | Noda et al. |
| 2007/0298667 | A1 | 12/2007 | Noda et al. |
| 2007/0298671 | A1 | 12/2007 | Noda et al. |
| 2007/0299416 | A1 | 12/2007 | Noda et al. |
| 2008/0010795 | A1 | 1/2008 | Mizutani et al. |
| 2008/0044622 | A1 | 2/2008 | Noda et al. |
| 2008/0044628 | A1 | 2/2008 | Noda et al. |
| 2008/0045915 | A1 | 2/2008 | Noda et al. |
| 2008/0085399 | A1 | 4/2008 | Noda et al. |
| 2008/0132136 | A1 | 6/2008 | Uematsu et al. |
| 2008/0147024 | A1 | 6/2008 | Potts et al. |
| 2008/0200894 | A1 | 8/2008 | Gatto et al. |
| 2009/0221978 | A1 | 9/2009 | Gatto et al. |
| 2009/0282660 | A1 | 11/2009 | Noda et al. |
| 2010/0069874 | A1 | 3/2010 | Noda et al. |
| 2010/0137824 | A1 | 6/2010 | Uematsu et al. |
| 2010/0191207 | A1 | 7/2010 | Oba et al. |
| 2011/0319851 | A1 | 12/2011 | Kudo et al. |
| 2012/0045620 | A1 | 2/2012 | Oba et al. |
| 2012/0123365 | A1* | 5/2012 | Pan ..................... A61K 8/0208 604/367 |
| 2012/0141742 | A1 | 6/2012 | Yamaguchi et al. |
| 2012/0177889 | A1 | 7/2012 | Uematsu et al. |
| 2012/0196091 | A1 | 8/2012 | Mizutani et al. |
| 2013/0034686 | A1 | 2/2013 | Mitsuno |
| 2013/0137328 | A1 | 5/2013 | Mitsuno |
| 2013/0226123 | A1 | 8/2013 | Kudo et al. |

FOREIGN PATENT DOCUMENTS

| | | |
|---|---|---|
| EP | 1362568 | 11/2003 |
| EP | 1371379 A1 | 12/2003 |
| EP | 2036521 | 3/2009 |
| EP | 2433602 | 3/2012 |
| GB | 2262235 | 6/1993 |
| JP | S57-17081 | 4/1982 |
| JP | S64-34365 | 2/1989 |
| JP | S64-56051 | 3/1989 |
| JP | H01-158954 | 6/1989 |
| JP | H02-152920 | 6/1990 |
| JP | H02-229255 | 9/1990 |
| JP | H05-154176 | 6/1993 |
| JP | H06-5614 | 1/1994 |
| JP | H06-502104 | 3/1994 |
| JP | H07-84697 | 9/1995 |
| JP | H08-510665 | 11/1996 |
| JP | H08-322879 | 12/1996 |
| JP | H10-95810 | 4/1998 |
| JP | H10-510743 | 10/1998 |
| JP | H11-512643 A | 11/1999 |
| JP | 2000-510376 | 8/2000 |
| JP | 3091283 | 9/2000 |
| JP | 2000-512886 | 10/2000 |
| JP | 2001-095845 | 4/2001 |
| JP | 2001-129019 | 5/2001 |
| JP | 2001-328191 | 11/2001 |
| JP | 2002-508693 | 3/2002 |
| JP | 3262172 | 3/2002 |
| JP | 2002-528174 A | 9/2002 |
| JP | 2002-537904 | 11/2002 |
| JP | 2003-024372 | 1/2003 |
| JP | 2003-052750 | 2/2003 |
| JP | 2004-500908 | 1/2004 |
| JP | 2004-049529 | 2/2004 |
| JP | 2005-504591 | 2/2005 |
| JP | 2005-095759 | 4/2005 |
| JP | 2005-193001 | 7/2005 |
| JP | 2005-525134 | 8/2005 |
| JP | 2006-501022 | 1/2006 |
| JP | 2006-510456 | 3/2006 |
| JP | 2006-115996 | 5/2006 |
| JP | 2006-255051 | 9/2006 |
| JP | 2006-280526 | 10/2006 |
| JP | 2007-014705 | 1/2007 |
| JP | 2007-97716 A | 4/2007 |
| JP | 2007-509695 | 4/2007 |
| JP | 2008-002034 | 1/2008 |
| JP | 2008-023311 | 2/2008 |
| JP | 2008-023365 | 2/2008 |
| JP | 2008-025078 | 2/2008 |
| JP | 2008-025079 | 2/2008 |
| JP | 2008-025080 | 2/2008 |
| JP | 2008-025081 | 2/2008 |
| JP | 2008-025082 | 2/2008 |
| JP | 2008-025083 | 2/2008 |
| JP | 2008-025084 | 2/2008 |
| JP | 2008-025085 | 2/2008 |
| JP | 2008-029830 | 2/2008 |
| JP | 2008-503323 | 2/2008 |
| JP | 2008-138340 | 6/2008 |
| JP | 2008-144322 | 6/2008 |
| JP | 2008-529721 | 8/2008 |
| JP | 2008-229032 | 10/2008 |
| JP | 2008-229033 | 10/2008 |
| JP | 2008-237569 | 10/2008 |
| JP | 2008-264084 | 11/2008 |
| JP | 2008-266813 | 11/2008 |
| JP | 2008-541943 | 11/2008 |
| JP | 2008-307179 | 12/2008 |
| JP | 2009-005767 | 1/2009 |
| JP | 2009-030218 | 2/2009 |
| JP | 2009-201878 A | 9/2009 |
| JP | 2009-297048 | 12/2009 |
| JP | 2010-088822 | 4/2010 |
| JP | 2010-518918 | 6/2010 |
| JP | 2010-148708 | 7/2010 |
| JP | 2010-526629 | 8/2010 |
| JP | 2010-279568 | 12/2010 |
| JP | 2010-285735 | 12/2010 |
| JP | 2011-038211 | 2/2011 |
| JP | 2011-067484 | 4/2011 |
| JP | 2011-072650 | 4/2011 |
| JP | 2011-074515 | 4/2011 |
| JP | 2011-080178 | 4/2011 |
| JP | 2011-510801 | 4/2011 |
| JP | 2011-104001 | 6/2011 |
| JP | 2011-104059 A | 6/2011 |
| JP | 2011-120696 | 6/2011 |
| JP | 4693847 | 6/2011 |
| JP | 2011-226010 | 11/2011 |

(56) References Cited

FOREIGN PATENT DOCUMENTS

| | | |
|---|---|---|
| JP | 2011-226011 | 11/2011 |
| JP | 2012-050626 | 3/2012 |
| JP | 5122007 | 1/2013 |
| WO | 93/01781 | 2/1993 |
| WO | 93/15701 A1 | 8/1993 |
| WO | 94/27539 | 12/1994 |
| WO | 96/19173 | 6/1996 |
| WO | 98/55158 | 12/1998 |
| WO | 99/00093 | 1/1999 |
| WO | 99/29274 | 6/1999 |
| WO | 00/24351 A1 | 5/2000 |
| WO | 01/45757 | 6/2001 |
| WO | 03/017900 | 3/2003 |
| WO | 03/028776 | 4/2003 |
| WO | 2004/030713 | 4/2004 |
| WO | 2004/058119 | 7/2004 |
| WO | 2005/044164 | 5/2005 |
| WO | 2006/009996 | 1/2006 |
| WO | 2006-130646 | 12/2006 |
| WO | 2008/072675 | 6/2008 |
| WO | 2008/101163 | 8/2008 |
| WO | 2008/139425 | 11/2008 |
| WO | 2008-149771 | 12/2008 |
| WO | 2009/102837 | 8/2009 |
| WO | 2012/133724 | 10/2012 |

OTHER PUBLICATIONS

International Search Report in corresponding PCT Application No. PCT/JP2013/054796 dated May 21, 2013, 1 page.
Written Opinion mailed Jul. 3, 2012 in corresponding International Application No. PCT/JP2012/058499.
International Search Report mailed Jul. 3, 2012 in corresponding International Application No. PCT/JP2012/058499.
Reply to Written Opinion dated Jan. 30, 2013, corresponds to International Application No. PCT/JP2012/058499.
Search Report mailed Jul. 17, 2012 in corresponding International Application No. PCT/JP2012/061505.
International International Search Report mailed Mar. 19, 2013 in corresponding International Application No. PCT/JP2012/082087.
International Search Report mailed Mar. 12, 2013 in corresponding International Application No. PCT/JP2012/082104.
International Search Report mailed Mar. 19, 2013 in corresponding International Application No. PCT/JP2013/054382.
International Search Report mailed Jan. 8, 2013 in corresponding International Application No. PCT/JP2012/075583.
International Search Report mailed Jul. 2, 2013 in corresponding International Application No. PCT/JP2013/058860.
International Search Report mailed Jul. 2, 2013 in corresponding International Application No. PCT/JP2013/058861.
International Search Report mailed Jul. 2, 2013 in corresponding International Application No. PCT/JP2013/058862.
International Search Report mailed Jun. 18, 2013 in corresponding International Application No. PCT/JP2013/058855.
International Search Report mailed Mar. 26, 2013 in corresponding International Application No. PCT/JP2012/082977.
International Search Report mailed May 14, 2013 in corresponding International Application No. PCT/JP2013/058836.
International Search Report mailed May 21, 2013 in corresponding International Application No. PCT/JP2013/058859.

* cited by examiner

Fig.6
(a)
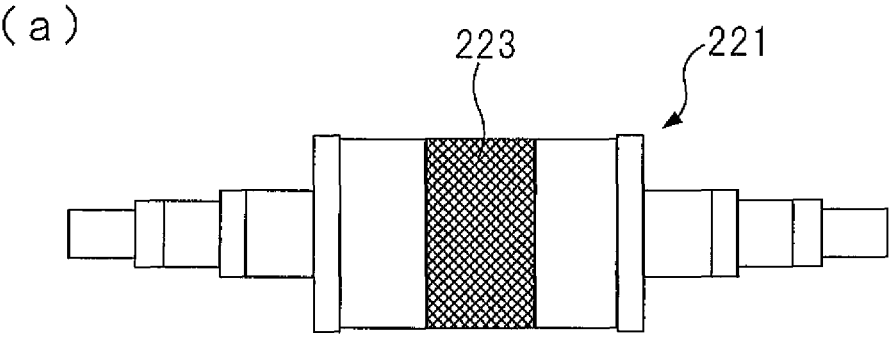
(b)
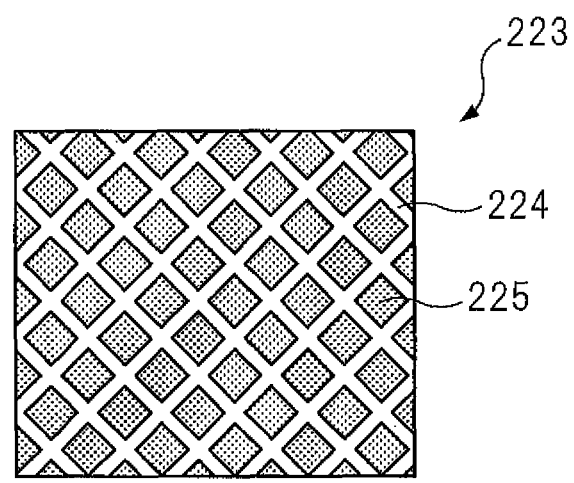
(c)
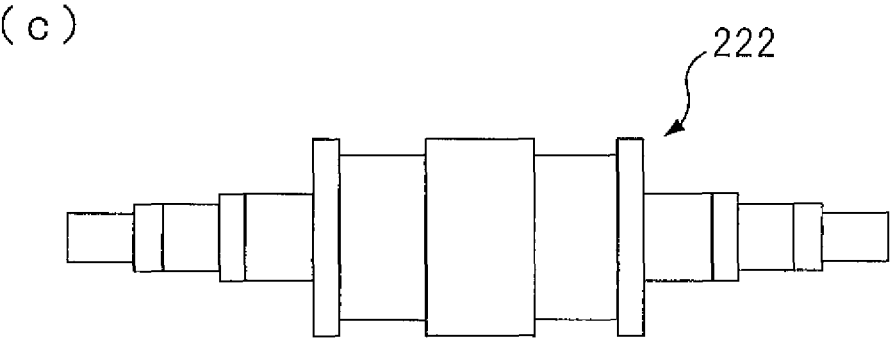

Fig.8
(a)
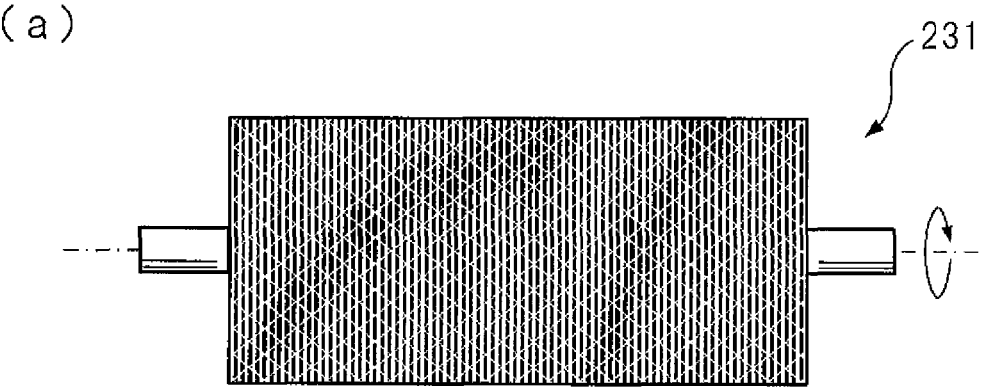
(b)
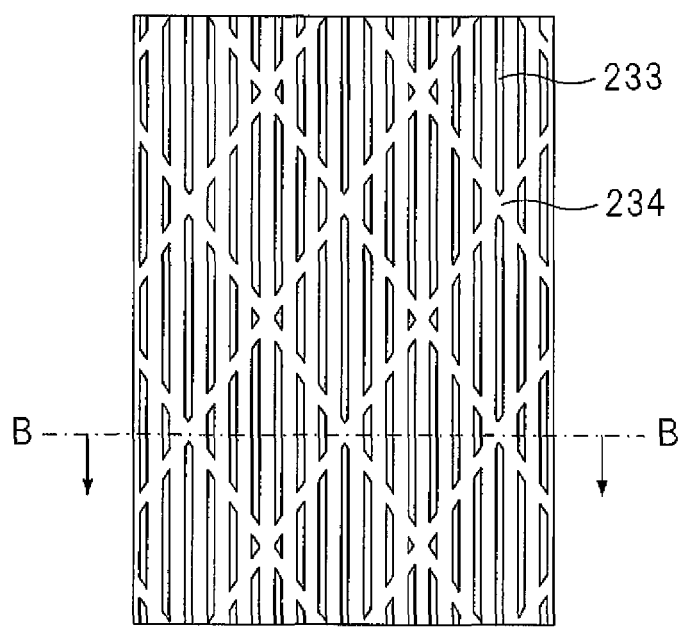
(c)
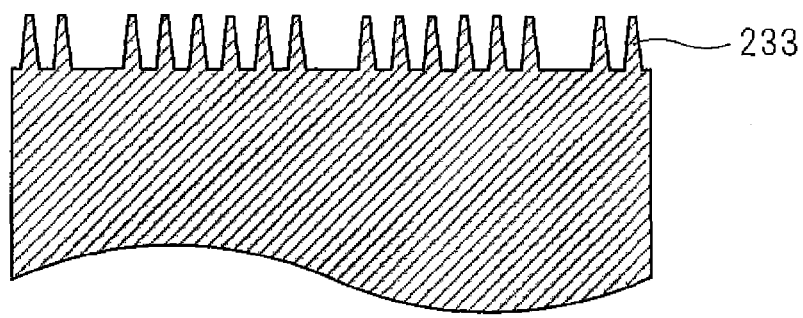

Fig.9
(a)
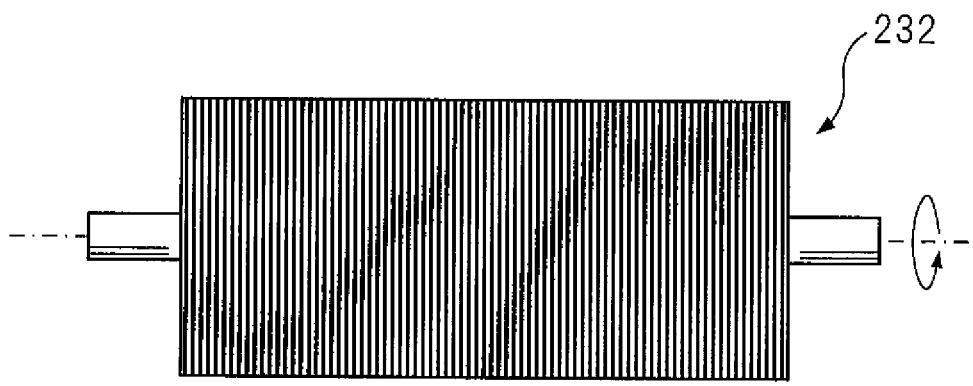
(b)
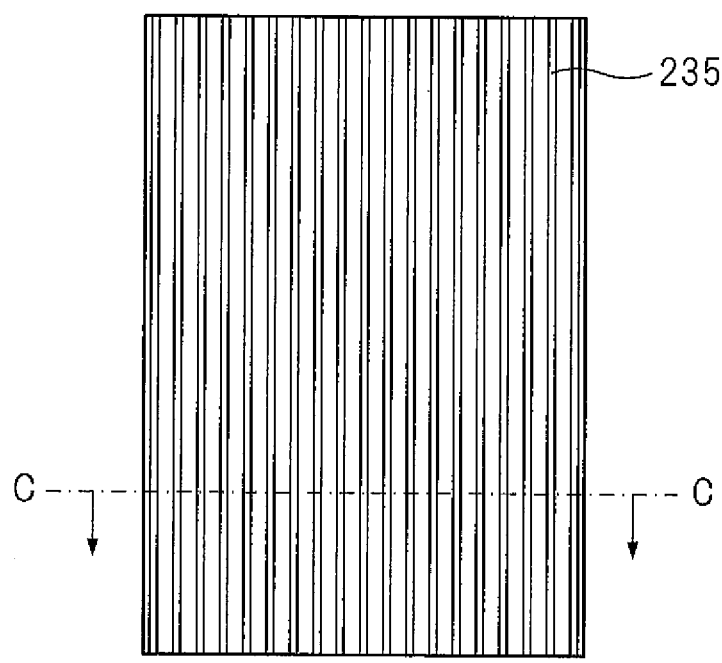
(c)
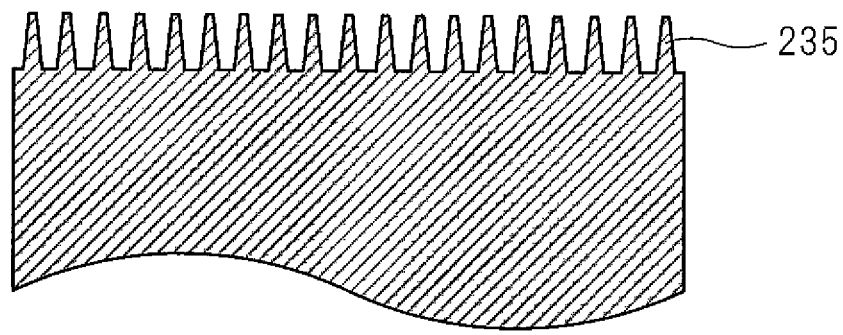

Fig.12
(a)
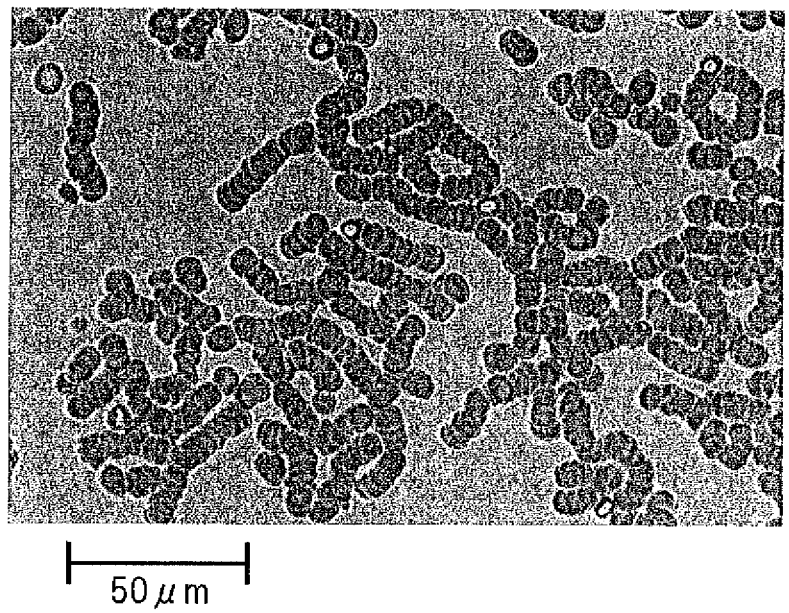
(b)
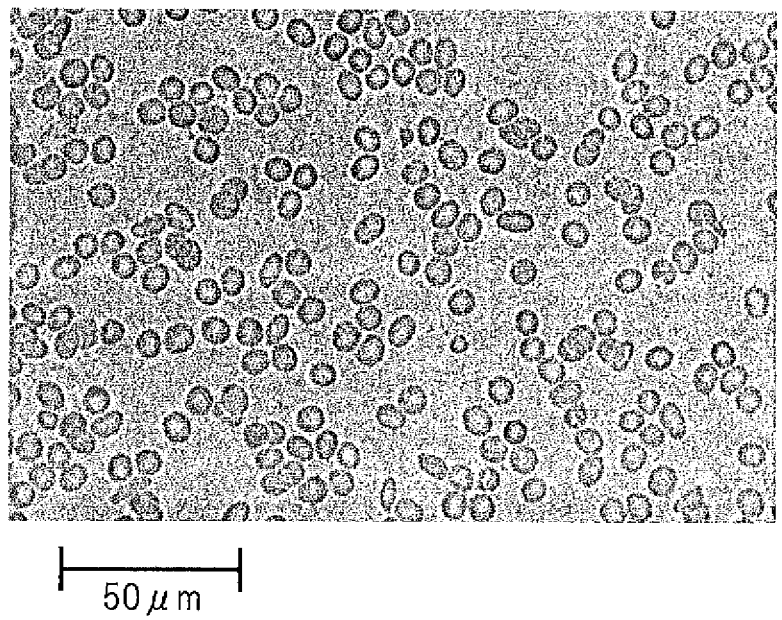

ABSORBENT ARTICLE

CROSS-REFERENCES TO RELATED APPLICATIONS

The present application is National Phase of International Application Number PCT/JP2013/054796 filed Feb. 25, 2013 and claims the priority of Japanese patent Application No. 2012-044439 filed Feb. 29, 2012, Japanese patent Application No. 2012-044524 filed Feb. 29, 2012, Japanese patent Application No. 2012-044575 filed Feb. 29, 2012 and Japanese patent Application No. 2012-082514 filed Mar. 30, 2012.

TECHNICAL FIELD

The present invention relates to an absorbent article, such as a sanitary napkin, panty liner, disposable diaper, incontinence pad or incontinence liner.

BACKGROUND ART

Conventional absorbent articles are provided with a liquid-permeable top sheet, a liquid-impermeable back sheet and an absorbent body provided between the top sheet and the back sheet, with liquids permeating through the top sheet being absorbed and retained by the absorbent body. Various modifications have also been implemented to prevent excessive compression of absorbent bodies during deformation of absorbent articles, which causes liquid that has been absorbed and retained in the absorbent body to flow back and leak from the top sheet (rewetting).

One such modification that has been proposed is to form a plurality of slits in the top sheet, so that the top sheet is essentially closed when in a state of non-tension, but the top sheet becomes stretched and perforated, thereby opening, when subjected to tension (Patent Literature (PTL) 1).

With the absorbent article described in PTL 1, however, tension during wear by the user after absorption of liquid excreta from the user results in opening of the slits formed in the top sheet and exposure of the absorbent body, the exposed absorbent body contacting the skin of the user and producing a sticky and unpleasant feel for the user.

CITATION LIST

Patent Literature

[PTL 1] Japanese Patent Public Inspection No. 2002-528174

DISCLOSURE OF THE INVENTION

Technical Problem

It is an object of the present invention to provide a novel absorbent article that prevents excessive compression on the absorbent body, caused by deformation of the absorbent article, and the rewetting that occurs as a result.

Solution to Problem

In order to solve the problems described above, the invention provides an absorbent article comprising a liquid-permeable sheet, a liquid-impermeable sheet and an absorbent body provided between the liquid-permeable sheet and the liquid-impermeable sheet, wherein the liquid-permeable sheet has an extensible region having an extendable bellows structure, and a flexible region encompassing the extensible region, which are formed in a liquid-receiving region that receives a liquid supplied to the liquid-permeable sheet.

When the absorbent article of the invention is folded at the liquid-receiving region of the liquid-permeable sheet and is deformed outward toward the liquid-receiving region side, the extensible region of the liquid-receiving region becomes extended, and therefore the absorbent body is not easily subjected to pressing force by the liquid-receiving region. Thus, excessive compression of the absorbent body due to deformation of the absorbent article, and the consequent rewetting, are prevented.

Also, when the absorbent article of the invention is deformed while the folding angle is varied (for example, when the folding angle of the absorbent article becomes an acute angle or an obtuse angle, by changes in the posture of the wearer of the absorbent article), elastic recoverability (repulsion) of the flexible region causes the liquid-permeable sheet to follow deformation of the absorbent article, and therefore distortion of the liquid-permeable sheet due to extension of the extensible region, and sticking of the distorted sheet to the skin, are prevented.

Effect of the Invention

According to the invention there is provided a novel absorbent article that prevents excessive compression on the absorbent body, caused by deformation of the absorbent article, and the rewetting that occurs as a result.

BRIEF DESCRIPTION OF DRAWINGS

FIG. 6 is a diagram illustrating a recess-forming roll to be used for production of a sanitary napkin according to an embodiment of the invention.

FIG. 8 is a diagram illustrating the upper roll of a stretching gear roll to be used for production of a sanitary napkin according to an embodiment of the invention.

FIG. 9 is a diagram illustrating the lower roll of a stretching gear roll to be used for production of a sanitary napkin according to an embodiment of the invention.

FIG. 12 is a pair of photomicrographs of menstrual blood containing and not containing a blood modifying agent.

DESCRIPTION OF EMBODIMENTS

Figure 1:
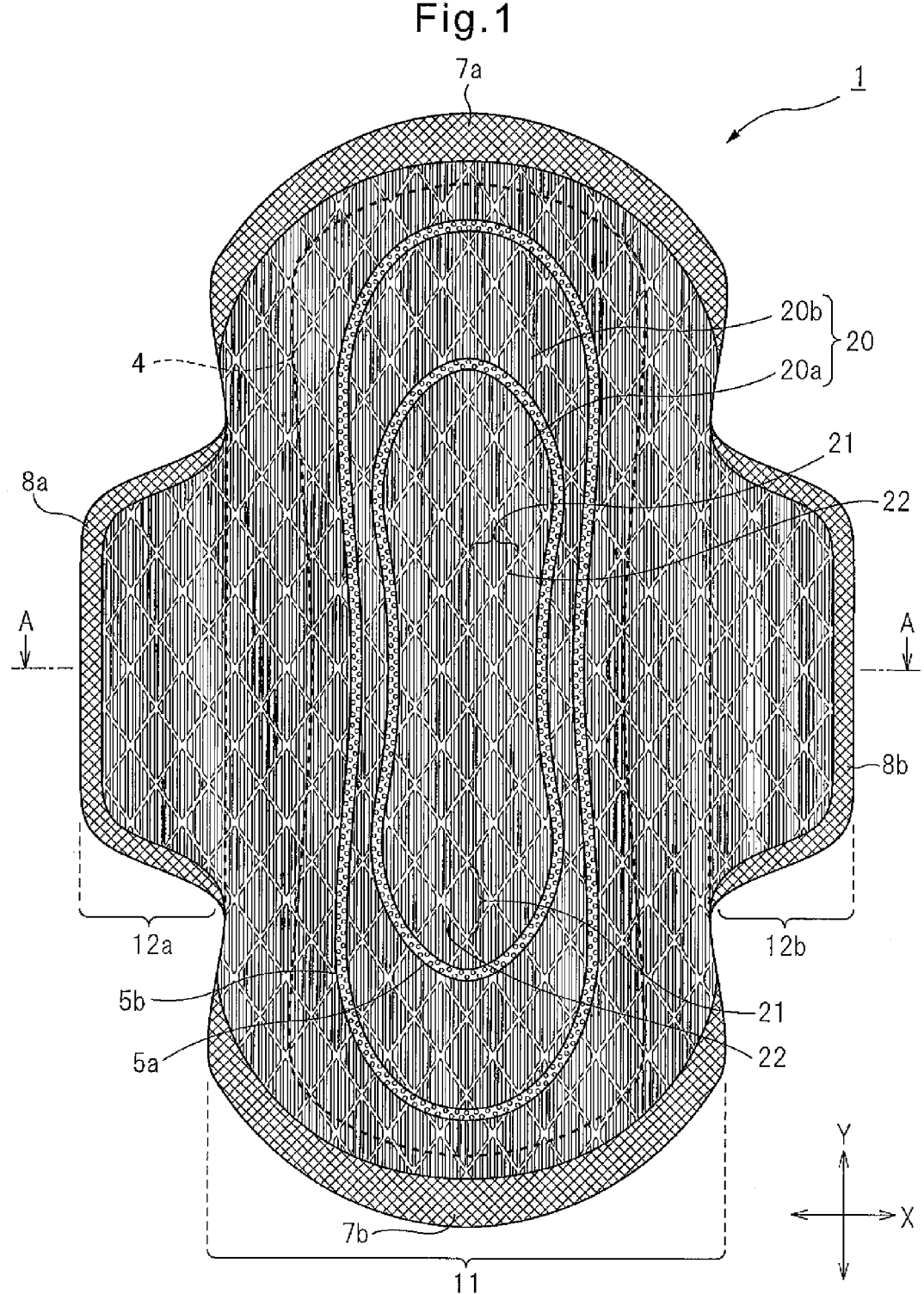
FIG. 1 is a plan view of a sanitary napkin according to an embodiment of the invention.

The absorbent article of the invention will now be described.

In the absorbent article of the invention, the liquid-receiving region is a region appropriately defined in the liquid-permeable sheet depending on the type and purpose of the absorbent article, and there are no particular restrictions on the location and area of the liquid-receiving region defined in the liquid-permeable sheet. The liquid-receiving region may be defined as roughly the same region as a region in which liquid is actually to be supplied, or it may be defined as a larger region, but from the viewpoint of preventing leakage of liquid to the exterior, it is preferably defined as a larger region than the region to which liquid is actually to be supplied.

In the absorbent article of the invention, the extensible region is a region that is extendable by extension of the bellows structure. The bellows structure has a repeating structure of mountain and valley folds, and thus is extendable in a surface direction of the extensible region. The bellows structure may also have a contractive property in addition to extensibility. However, even if the bellows structure has a contractive property, the bellows structure may not completely contract to its original state, depending on the quality of the bellows structure and the number of bellows, and will often remain in a slightly more extended state than the original state.

In the absorbent article of the invention, the flexible region is a region with elastic recoverability (repulsion) against deformation. The flexible region may undergo extension by force applied during deformation, but from the viewpoint of increasing elastic recoverability against deformation, it preferably undergoes essentially no extension by force applied during deformation.

The flexible region in the absorbent article of the invention encompasses all or part of the surrounding portion of the extensible region. From the viewpoint of effectively producing extension of the extensible region which prevents excessive compression of the absorbent body and elastic recoverability of the flexible region which prevents distortion of the liquid-permeable sheet, when the absorbent article is deformed outward, the flexible region preferably encompasses 30-100%, more preferably encompasses 50-100% and most preferably encompasses 100% of the entire surrounding portion of the extensible region.

In a preferred aspect of the absorbent article of the invention (Aspect 1), a plurality of extensible regions each having an extendable bellows structure are formed in the liquid-receiving region, and the flexible region encompasses each of the extensible regions. According to Aspect 1, extension of the extensible regions which prevents excessive compression of the absorbent body, and elastic recoverability of the flexible region which prevents distortion of the liquid-permeable sheet, are effectively produced when the absorbent article is deformed outward.

In a preferred aspect of Aspect 1 (Aspect 2), the flexible region is formed in a net-like pattern, and each of the extensible regions is formed on the inner side of a mesh unit of the net-like pattern. According to Aspect 2, a plurality of extensible regions, and a flexible region encompassing each of the extensible regions, are disposed, in order to effectively produce extension of the extensible regions which prevents excessive compression of the absorbent body, and elastic recoverability of the flexible region which prevents distortion of the liquid-permeable sheet, during outward deformation of the absorbent article.

In a preferred aspect of Aspect 2 (Aspect 3), the flexible region has roughly linear first regions laid out in a direction crossing a lengthwise direction of the absorbent article and aligned in an approximately parallel manner, and roughly linear second regions laid out in a direction crossing the first regions and aligned in an approximately parallel manner. According to Aspect 3, the net-like flexible region is disposed so as to effectively produce extension of the extensible regions which prevents excessive compression of the absorbent body, and elastic recoverability of the flexible region which prevents distortion of the liquid-permeable sheet, during outward deformation of the absorbent article.

In a preferred aspect of the absorbent article of the invention (Aspect 4), the bellows structure has mountain and valley folds that are laid out in a lengthwise direction of the absorbent article, are aligned in a widthwise direction of the absorbent article, and have a wavy cross-section along the widthwise direction. According to Aspect 4, the bellows structure extends in the widthwise direction of the absorbent article when the absorbent article is folded along the lengthwise direction and thus deformed outward toward the liquid-receiving region side, and therefore excessive compression of the absorbent body due to the outward deformation, and consequent rewetting, are effectively prevented.

In a preferred aspect of the absorbent article of the invention (Aspect 5), a liquid permeation hole is formed in the extensible region, and no liquid permeation hole is formed in the flexible region. According to Aspect 5, the liquid permeation hole is formed in the extensible region which is not directly subjected to tension when the absorbent article is deformed outward, while no liquid permeation hole is formed in the flexible region which is directly subjected to tension, and therefore stretching of the liquid permeation hole by tension and exposure of the absorbent body are prevented.

In a preferred aspect of the absorbent article of the invention (Aspect 6), a compressed groove is formed at the perimeter of the liquid-receiving region. The compressed groove is a recess formed by integrating the perimeter of the liquid-receiving region and the absorbent body by compression. According to Aspect 6, the absorbent article easily and stably undergoes outward deformation starting from the compressed groove, and therefore extension of the extensible region which prevents excessive compression of the absorbent body, and elastic recoverability of the flexible region which prevents distortion of the liquid-permeable sheet, are effectively produced during outward deformation of the absorbent article.

In a preferred aspect of the absorbent article of the invention (Aspect 7), the liquid-permeable sheet comprises a blood modifying agent with an IOB of 0.00-0.60, a melting point of 45° C. or less, and a water solubility of 0.00-0.05 g in 100 g of water at 25° C. According to Aspect 7, when a menstrual blood is a liquid to be absorbed by the absorbent article, the blood modifying agent has contact with a menstrual blood that has been discharged onto the liquid-permeable sheet, and makes property modification of the menstrual blood. This helps prevent residue of highly viscous menstrual blood into the liquid-permeable sheet, reduces stickiness of the liquid-permeable sheet, and improves the surface drying property of the liquid-permeable sheet, while also leaving less of a visually unpleasant image for the wearer.

In a preferred aspect of Aspect 7 (Aspect 8), the blood modifying agent is selected from the group consisting of following items (i)-(iii) and combinations thereof:
 (i) a hydrocarbon;
 (ii) a compound having (ii-1) a hydrocarbon moiety, and (ii-2) one or more, same or different groups selected from the group consisting of carbonyl group (—CO—) and oxy group (—O—) inserted between a C—C single bond of the hydrocarbon moiety; and (iii) a compound having (iii-1) a hydrocarbon moiety, (iii-2) one or more, same or different groups selected from the group consisting of carbonyl group (—CO—) and oxy group (—O—) inserted between a C—C single bond of the hydrocarbon moiety, and (iii-3) one or more, same or different groups selected from the group consisting of carboxyl group (—COOH) and hydroxyl group (—OH) substituted for a hydrogen of the hydrocarbon moiety;

with the proviso that when 2 or more oxy groups are inserted in the compound of (ii) or (iii), the oxy groups are not adjacent.

In a preferred aspect of Aspect 7 or 8 (Aspect 9), the blood modifying agent is selected from the group consisting of following items (i')-(iii') and combinations thereof:

(i') a hydrocarbon;

(ii') a compound having (ii'-1) a hydrocarbon moiety, and (ii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety; and (iii') a compound having (iii'-1) a hydrocarbon moiety, (iii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety, and (iii'-3) one or more, same or different groups selected from the group consisting of carboxyl group (—COOH) and hydroxyl group (—OH) substituted for a hydrogen on the hydrocarbon moiety;

with the proviso that when 2 or more same or different bonds are inserted in a compound of (ii') or (iii'), the bonds are not adjacent.

In a preferred aspect of Aspects 7 to 9 (Aspect 10), the blood modifying agent is selected from the group consisting of following items (A)-(F) and combinations thereof:

(A) an ester of (A1) a compound having a chain hydrocarbon moiety and 2-4 hydroxyl groups substituted for hydrogens on the chain hydrocarbon moiety, and (A2) a compound having a chain hydrocarbon moiety and 1 carboxyl group substituted for a hydrogen on the chain hydrocarbon moiety;

(B) an ether of (B1) a compound having a chain hydrocarbon moiety and 2-4 hydroxyl groups substituted for hydrogens on the chain hydrocarbon moiety, and (B2) a compound having a chain hydrocarbon moiety and 1 hydroxyl group substituted for a hydrogen on the chain hydrocarbon moiety;

(C) an ester of (C1) a carboxylic acid, hydroxy acid, alkoxy acid or oxoacid comprising a chain hydrocarbon moiety and 2-4 carboxyl groups substituted for hydrogens on the chain hydrocarbon moiety, and (C2) a compound having a chain hydrocarbon moiety and 1 hydroxyl group substituted for a hydrogen on the chain hydrocarbon moiety;

(D) a compound having a chain hydrocarbon moiety and one bond selected from the group consisting of ether bonds (—O—), carbonyl bonds (—CO—), ester bonds (—COO—) and carbonate bonds (—OCOO—) inserted between a C—C single bond of the chain hydrocarbon moiety;

(E) a polyoxy $C_2$-$C_6$ alkylene glycol, or its ester or ether; and (F) a chain hydrocarbon.

In a preferred aspect of Aspects 7 to 10 (Aspect 11), the blood modifying agent is selected from the group consisting of ($a_1$) an ester of a chain hydrocarbon tetraol and at least one fatty acid, ($a_2$) an ester of a chain hydrocarbon triol and at least one fatty acid, ($a_3$) an ester of a chain hydrocarbon diol and at least one fatty acid, ($b_1$) an ether of a chain hydrocarbon tetraol and at least one aliphatic monohydric alcohol, ($b_2$) an ether of a chain hydrocarbon triol and at least one aliphatic monohydric alcohol, ($b_3$) an ether of a chain hydrocarbon diol and at least one aliphatic monohydric alcohol, ($c_1$) an ester of a chain hydrocarbon tetracarboxylic acid, hydroxy acid, alkoxy acid or oxoacid with 4 carboxyl groups, and at least one aliphatic monohydric alcohol, ($c_2$) an ester of a chain hydrocarbon tricarboxylic acid, hydroxy acid, alkoxy acid or oxoacid with 3 carboxyl groups, and at least one aliphatic monohydric alcohol, ($c_3$) an ester of a chain hydrocarbon dicarboxylic acid, hydroxy acid, alkoxy acid or oxoacid with 2 carboxyl groups, and at least one aliphatic monohydric alcohol, ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, ($d_4$) a dialkyl carbonate, ($e_1$) a polyoxy $C_2$-$C_6$ alkylene glycol, ($e_2$) an ester of a polyoxy $C_2$-$C_6$ alkylene glycols and at least one fatty acid, ($e_3$) an ether of a polyoxy $C_2$-$C_6$ alkylene glycol and at least one aliphatic monohydric alcohol, ($e_4$) an ester of a polyoxy $C_2$-$C_6$ alkylene glycols and a chain hydrocarbon tetracarboxylic acid, chain hydrocarbon tricarboxylic acid or chain hydrocarbon dicarboxylic acid, ($e_5$) an ether of a polyoxy $C_2$-$C_6$ alkylene glycol and a chain hydrocarbon tetraol, chain hydrocarbon triol or chain hydrocarbon diol, and ($f_1$) a chain alkane, and combinations thereof.

Two or more of Aspects 1 to 11 may be combined for the absorbent article of the invention.

There are no particular restrictions on the type or purpose of the absorbent article of the invention, and for example, absorbent articles include sanitary products and sanitary articles such as sanitary napkins, panty liners, disposable diapers, incontinence pads, incontinence liners and perspiration sheets, which may be for humans or animals other than humans, such as pets. There are no particular restrictions on the liquid to be absorbed by the absorbent article, and for example, it may be liquid excreta or body fluid of the user.

Embodiments of the absorbent article of the invention will now be described, using a sanitary napkin as an example.

<First Embodiment>

Figure 2:
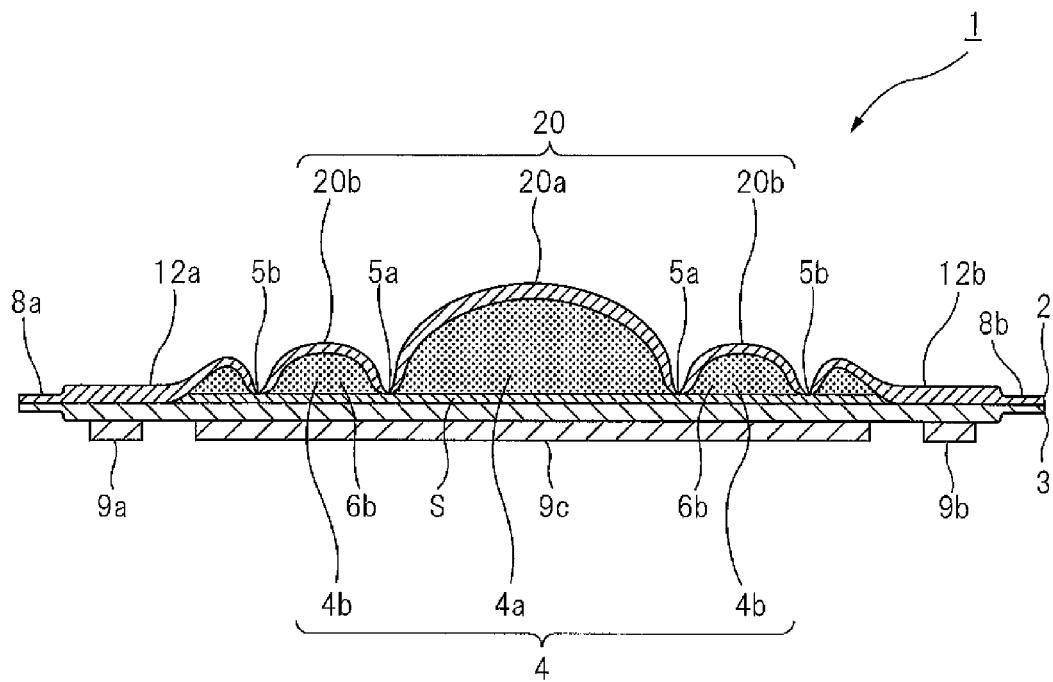
FIG. 2 is a schematic cross-sectional view showing a cross-section of FIG. 1 along line A-A.

As shown in FIG. 1 and FIG. 2, a sanitary napkin 1 according to the first embodiment comprises a liquid-permeable top sheet 2, a liquid-impermeable back sheet 3, and an absorbent body 4 formed between the top sheet 2 and the back sheet 3.

In FIG. 1, the X-axial direction is the widthwise direction of the sanitary napkin 1, the Y-axial direction is the lengthwise direction of the sanitary napkin 1, and the direction of the plane extending in the X-axial and Y-axial directions corresponds to the planar direction of the sanitary napkin 1. The same applies to the other drawings as well. FIG. 2 is a schematic cross-sectional view, omitting bellows structures 210 formed in the top sheet 2.

The sanitary napkin 1 is worn by a user to absorb liquid excreta (such as menstrual blood). The user wears it in such a manner that the top sheet 2 is on the skin side of the user, and the back sheet 3 is located on the side of the clothing (underwear) of the user. The liquid excreta passes through the top sheet 2 and permeates the absorbent body 4, and is absorbed and retained in the absorbent body 4. Leakage of liquid excreta that has been absorbed into the absorbent body 4 is prevented by the back sheet 3.

As shown in FIG. 1 and FIG. 2, the top sheet 2 and back sheet 3 have their edges bonded together in the lengthwise direction by seal sections 7a, 7b, forming the body section 11, while having their edges bonded together in the widthwise direction by seal sections 8a, 8b, forming roughly rectangular wing sections 12a, 12b that extend out in the widthwise direction from the body section 11. By bonding the perimeters of the top sheet 2 and back sheet 3 with the seal sections 7a, 7b, 8a, 8b, separation of both sheets during deformation of the sanitary napkin 1 can be prevented.

The shape of the body section 11 may be appropriately modified within a range suitable for the female body and underwear, and for example, it may be roughly rectangular, roughly elliptical or roughly gourd-shaped. The dimension of extension in the lengthwise direction of the body section 11 is preferably 100 to 500 mm and more preferably 150 to 350 mm, while the dimension of extension in the widthwise direction of the body section 11 is preferably 30 to 200 mm and more preferably 40 to 180 mm.

The bonding method for the seal sections 7a, 7b, 8a, 8b may be embossing, ultrasonic waves or a hot-melt adhesive. In order to increase the bonding strength, two or more different bonding methods may be combined (for example, bonding with a hot-melt adhesive followed by embossing).

As an example of embossing, the top sheet 2 and back sheet 3 may be passed together between a patterned embossing roll and a flat roll, for embossing (a method known as round sealing). By heating the embossing roll and/or flat roll by this method, each sheet is softened so that the seal sections become more distinct. Examples of emboss patterns include lattice-like patterns, zigzag patterns and wavy patterns. In order to impede bending of the sanitary napkin 1 at the borders of the seal sections, the emboss pattern is preferably intermittently elongated.

Examples of hot-melt adhesives include pressure-sensitive adhesives and heat-sensitive adhesives composed mainly of rubber-based compounds such as styrene-ethylene-butadiene-styrene (SEBS), styrene-butadiene-styrene (SBS) or styrene-isoprene-styrene (SIS), or composed mainly of olefin-based compounds such as linear low-density polyethylene; and water-sensitive adhesives comprising water-soluble polymers (such as polyvinyl alcohol, carboxylmethyl cellulose and gelatin) or water-swelling polymers (such as polyvinyl acetate and sodium polyacrylate). Specific examples of adhesive coating methods include spiral coating application, coater application, curtain coater application and summit-gun coating.

As shown in FIG. 2, pressure-sensitive adhesive sections 9a, 9b are provided on the clothing side of the back sheet 3 forming the wing sections 12a, 12b, and a pressure-sensitive adhesive section 9c is provided on the clothing side of the back sheet 3 forming the body section 11. The pressure-sensitive adhesive section 9c is attached to the crotch section of underwear, while the wing sections 12a, 12b are folded toward the outer wall of the underwear and the pressure-sensitive adhesive sections 9a, 9b are attached to the crotch section of the underwear, thereby stably anchoring the sanitary napkin 1 to the underwear.

Examples of pressure-sensitive adhesives to be used in the pressure-sensitive adhesive sections 9a, 9b, 9c include styrene-based polymers such as styrene-ethylene-butylene-styrene block copolymer, styrene-butylene polymer, styrene-butylene-styrene block copolymer and styrene-isobutylene-styrene copolymer; tackifiers such as C5 petroleum resins, C9 petroleum resins, dicyclopentadiene-based petroleum resins, rosin-based petroleum resins, polyterpene resins and terpenephenol resins; monomer plasticizers such as tricresyl phosphate, dibutyl phthalate and dioctyl phthalate; and polymer plasticizers such as vinyl polymer and polyester.

The top sheet 2 is provided on the side in contact with the skin of the user, to improve the feel on the skin when the sanitary napkin 1 is worn by the user.

As shown in FIG. 1 and FIG. 2, there is defined in the top sheet 2 an excreta-receiving region 20 which receives supply of liquid excreta from the user. The excreta-receiving region 20 includes an excretory opening contact region 20a with which the excretory opening of the user (for example, the labia minora, labia majora or vaginal opening) contacts, and a peripheral region 20b located in the surrounding portion of the excretory opening contact region 20a, the length of the excreta-receiving region 20 being usually 50 to 200 mm and preferably 70 to 150 mm, and the width being usually 10 to 80 mm and preferably 20 to 50 mm. In order to increase the absorption property for liquid excreta, the excretory opening contact region 20a is wider than the region in which the excretory opening of the user actually contacts. The peripheral region 20b is disposed in the surrounding portion of the excretory opening contact region 20a, in order to prevent leakage of liquid excreta that has not been absorbed from the excretory opening contact region 20a. The peripheral region 20b effectively prevents leakage of liquid excreta that has not been absorbed from the excretory opening contact region 20a, and especially leakage from the widthwise direction of the sanitary napkin 1.

The top sheet 2 is composed of a flexible material. The flexible material is a material with elastic recoverability (repulsion) against deformation. The flexible material may undergo extension by force applied during deformation, but from the viewpoint of increasing elastic recoverability against deformation, it preferably undergoes essentially no extension by force applied during deformation.

Examples of flexible materials include synthetic resins, with examples of synthetic resins including copolymers of olefins with other monomers such as acrylic acid esters and vinyl acetate; polyolefins such as low-density polyethylene, linear low-density polyethylene, high-density polyethylene and polypropylene; polyesters such as polyethylene terephthalate; polyamides; and cellulose acetate, among which copolymers of olefins with other monomers, and polyolefins, are preferred from the viewpoint of high flexibility and low irritation to skin. The flexible material may be a mixed material of two or more different synthetic resins, such as a mixed material of 20-60% low-density polyethylene, 30-60% linear low-density polyethylene and 5-20% high-density polyethylene.

Figure 3:
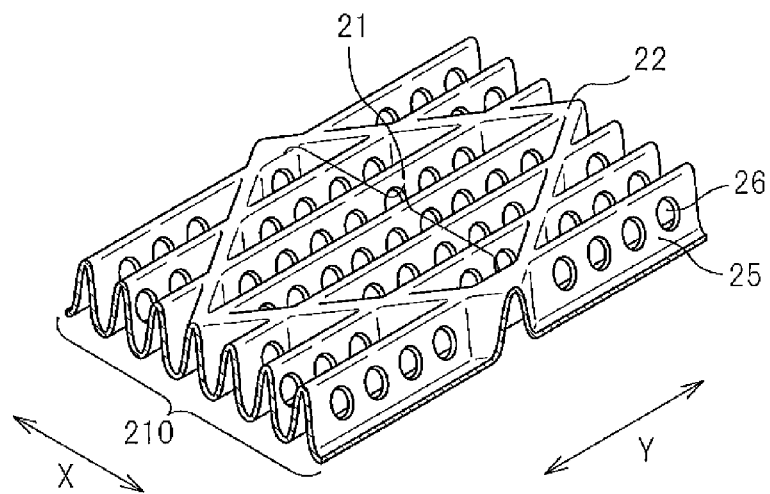
FIG. 3 is a partial cutaway perspective view showing a magnified view of an extensible region and flexible region of a top sheet in a sanitary napkin according to an embodiment of the invention.

As shown in FIG. 1 and FIG. 3, flexible regions 22 are formed in the top sheet 2 in a net-like pattern over roughly the entirety including the excreta-receiving region 20, and each of extensible regions 21 is formed on the inner side of a mesh unit (a mesh cell) of the net-like pattern. The extensible regions 21 have extensibility due to extension of the bellows structures 210, while the flexible regions 22 have flexibility (elastic recoverability against deformation) due to the flexible material composing the top sheet 2. As shown in FIG. 3, the flexible regions 22 are generally flat, and do not have the structural extensibility of the extensible regions 21.

As shown in FIG. 3, throughout the extensible regions 21 there are formed bellows structures 210 with a repeating structure of mountain and valley folds. By stretching the mountain and valley folds of the bellows structures 210, the extensible regions 21 are extendable in the surface direction of the extensible regions 21. In FIG. 3, assuming the top sheet 2 side to be facing upward and the back sheet 3 side to be facing downward, the upward-facing protrusions are the mountain folds, and the downward-facing protrusions are the valley folds.

As shown in FIG. 1 and FIG. 3, the mountain and valley folds of the bellows structures 210 are laid out in the lengthwise direction of the sanitary napkin 1, while being aligned in the widthwise direction of the sanitary napkin 1. This configuration effectively produces extension of the bellows structures 210 (extension in the widthwise direction of the sanitary napkin 1), which prevents excessive compression of the absorbent body 4, when the sanitary napkin 1 is folded along the lengthwise direction, being deformed outward toward the top sheet 2 side.

As shown in FIG. 3, the cross-section of the bellows structures 210 along the widthwise direction of the sanitary napkin 1 is essentially wavy. The term "essentially wavy" includes modified forms such as a straightened form of the curve of a U-shape, a block-like U-shape, and more V-like U-shapes.

The widths of the uppermost sections of the mountain folds and the widths of the lowermost sections of the valley folds will usually be 0.1 to 2.0 mm and are preferably 0.2 to 1.5 mm, the heights of the mountain folds and the depths of the valley folds will usually be 0.3 to 3.0 mm and are preferably 0.5 to 1.5 mm, and the widths between the uppermost sections of adjacent mountain folds and the widths between the lowermost sections of adjacent valley folds will usually be 0.3 to 3.0 mm and are preferably 0.5 to 2.0 mm.

The bellows structures 210 may also have a contractive property in addition to extensibility. However, even if the bellows structures 210 have a contractive property, the extended bellows structures 210 may not completely contract to their original state, depending on the quality of the bellows structures 210 and the number of bellows, often remaining in a slightly more extended state than the original state.

When the bellows structures 210 are to be given a contractive property, it is sufficient to mix an elastomer material with the flexible material composing the top sheet 2. Examples of elastomers include polyester-based, urethane-based, olefin-based, styrene-based and polyamide-based thermoplastic elastomers, and low-density polyethylene or ethylene-α-olefin copolymers using metallocene catalysts, as well as combinations of the foregoing.

Examples of polyester-based elastomers include ones that contain an amorphous polyether, aliphatic polyester or the like as a soft segment in an aromatic polyester hard segment, examples of urethane-based elastomers include polyurethanes comprising a polyester, low molecular glycol or methylenebisphenyl isocyanate as a thermoplastic elastomer, examples of olefin-based elastomers include random copolymers of ethylene and α-olefins, and random copolymers of ethylene, α-olefins and dienes, examples of styrene-based elastomers include block copolymers such as SEBS, SIS, SEPS and SBS, and polyamide-based elastomers include ones containing nylon as the hard segment and a polyester or polyol as the soft segment.

As shown in FIG. 1 and FIG. 3, the flexible regions 22 have m regions that are laid out in a direction crossing the lengthwise direction of the sanitary napkin 1 and are roughly linear and aligned in an approximately parallel manner (hereunder referred to as "regions $A_{1-m}$"), and n regions that are laid out in a direction crossing the regions $A_{1-m}$ and are roughly linear and aligned in an approximately parallel manner (hereunder referred to as "regions $B_{1-n}$"). The flexible regions 22 are formed in a net-like pattern by intersection of the regions $A_{1-m}$ and $B_{1-n}$.

The angle $\alpha_1$ at which the regions $A_{1-m}$ cross the lengthwise direction of the sanitary napkin 1 will usually be $1°\leq\alpha_1\leq90°$, preferably $10°\leq\alpha_1\leq80°$ and even more preferably $30°\leq\alpha_1\leq60°$. The angle $\alpha_2$ at which the regions $B_{1-n}$ cross the lengthwise direction of the sanitary napkin 1 (with the proviso that the angle at which the regions $B_{1-n}$ cross the regions $A_{1-m}$ is $\alpha_1+\alpha_2$) will usually be $1°\leq\alpha_2\leq90°$, preferably $10°\leq\alpha_2\leq80°$ and even more preferably $30°\leq\alpha_2\leq60°$. However, $\alpha_1$ and $\alpha_2$ are selected so that $\alpha_1+\alpha_2$ is not 180°. If $\alpha_1$ and $\alpha_2$ are within these ranges, the regions $A_{1-m}$ and $B_{1-n}$ will be located on both sides sandwiching the lengthwise direction of the sanitary napkin 1, and therefore when the sanitary napkin 1 folds along the lengthwise direction being deformed outward, the repulsion (recoverability) of the flexible regions 22 against outward deformation is more easily exhibited, and the dimensions of each mesh unit necessary to form the bellows structures 210 in the extensible regions 21 is ensured.

The number (m) of regions $A_{1-m}$ and the number (n) of regions $B_{1-n}$ are not limited to the numbers shown in FIG. 1, and they may be appropriately modified according to the size of the sanitary napkin 1. The numbers m and n may have identical or different numerical values, and the numerical ranges for m and n will usually be 4-60, preferably 8-40 and even more preferably 10-35.

The widths of the regions for the regions $A_{1-m}$ and $B_{1-n}$ will usually be 0.1 to 5 mm, preferably 0.3 to 3 mm and even more preferably 0.5 to 2 mm. If the widths of the regions $A_{1-m}$ and $B_{1-n}$ are within this range, the repulsion (recoverability) of the flexible regions 22 against outward deformation will be more easily exhibited, and the dimensions of each mesh unit necessary to form the bellows structures 210 in the extensible regions 21 will be ensured.

As shown in FIG. 1 and FIG. 3, the shapes of the mesh units formed by intersection of the regions $A_{1-m}$ and $B_{1-n}$ are roughly rhomboid. As a modification of this embodiment, the shapes of the mesh units may be approximately polygonal, such as roughly triangular, roughly quadrilateral or roughly pentagonal. Approximately polygonal shapes include modified forms of these shapes with rounded corners, or curves instead of the straight lines forming the sides. As a modification to this embodiment, the regions $A_{1-m}$ and $B_{1-n}$ may be curved, the shapes of the mesh units being roughly circular or ellipsoid.

The sizes of the mesh units in the lengthwise direction and the widthwise direction of the sanitary napkin 1 will usually be 3 to 40 mm, preferably 5 to 30 mm and even more preferably 10 to 20 mm. If the size of the mesh units are within this range, the repulsion (recoverability) of the flexible regions 22 against outward deformation will be more easily exhibited, and the dimensions of each mesh unit necessary to form the bellows structures 210 in the extensible regions 21 will be ensured.

The total number of mountain and valley folds formed in each mesh unit will usually be at least 3, and is preferably 5-19 and even more preferably 7-15. However, this is with the proviso that the total number of mountain and valley folds is odd. If the total number of mountain and valley folds of the bellows structures 210 is within this range, extension of the bellows structures 210 that prevents excessive compression of the absorbent body 4 will be effectively produced when the sanitary napkin 1 is deformed outward.

As shown in FIG. 1 and FIG. 3, the flexible regions 22 encompass the entire surrounding portions of the extensible regions 21, with connection between adjacent extensible regions being blocked by the flexible regions 22. As an additional modification to this embodiment, some of the surrounding portions of the extensible regions 21 may be encompassed by flexible regions 22. In this case, from the viewpoint of effectively producing extension of the bellows structures 210 which prevents excessive compression of the absorbent body 4 and elastic recoverability of the flexible regions 22 which prevents distortion of the top sheet 2, during outward deformation of the sanitary napkin 1, the flexible regions 22 preferably encompass at least 30% and more preferably encompass at least 50% of the entire surrounding portion of the extensible regions.

As shown in FIG. 1 and FIG. 3, the flexible regions 22 are connected with the perimeters of the extensible regions 21. Also, as shown in FIG. 3, the flexible regions 22 are connected with the uppermost sections of the mountain folds in the bellows structures 210. As an additional modification to this embodiment, the flexible regions 22 may be connected with the lowermost sections of the valley folds in the bellows structures 210. However, from the viewpoint of giving the top sheet 2 a smooth feel on the skin when the flexible regions 22 are on the skin surface side, the flexible regions 22 are preferably connected with the uppermost sections of the mountain folds in the bellows structures 210, as shown in FIG. 3.

As shown in FIG. 3, a plurality of liquid permeation holes 26 are formed in the top sheet 2, and liquid excreta can permeate to the absorbent body 4 through the liquid permeation holes 26. As shown in FIG. 3, the liquid permeation holes 26 are formed in the extensible regions 21 that are not directly subjected to tension during outward deformation (the side sections 25 of the bellows structures 210 which connect the uppermost sections of the mountain folds and the lowermost sections of the valley folds) within the excreta-receiving region 20 of the top sheet 2, but they are not formed in the flexible regions 22 that are not directly subjected to tension during outward deformation. Thus, the liquid permeation holes 26 are not easily stretched by tension, and this prevents the absorbent body 4 that has absorbed liquid excreta from being exposed and contacting the skin of the user, and causing a sticky and unpleasant feel for the user.

The open area of each liquid permeation hole 26 is preferably 0.001 to 1 $mm^2$ and even more preferably 0.01 to 0.1 $mm^2$. If the open area of each liquid permeation hole 26 is smaller than 0.001 $mm^2$ it may be difficult for liquid excreta to penetrate, and if it exceeds 1 $mm^2$, liquid excreta that has been absorbed into the absorbent body 4 may flow back through the liquid permeation holes 26, or the concealing property of the top sheet 2 may be reduced.

The proportion of the total open area with respect to the area of the top sheet 2, i.e. the open area ratio of the top sheet 2, is preferably 5% to 20%. If the open area ratio of the top sheet 2 is lower than 5%, permeability of liquid excreta in the top sheet 2 may be poor, and if the open area ratio of the top sheet 2 is higher than 20%, body fluid that has been absorbed into the absorbent body 4 may flow back through the liquid permeation holes 26, or liquid excreta that has been absorbed into the absorbent body 4 may become visible through the liquid permeation holes 26.

The thickness and basis weight of the top sheet 2 may be appropriately adjusted from the viewpoint of formability of the bellows structures 210 of the extensible regions 21, and flexibility of the flexible regions 22. The basis weight of the top sheet 2 will usually be 10 $g/m^2$ or greater (for example, 10 to 40 $g/m^2$) and preferably 20 to 30 $g/m^2$, and the thickness of the top sheet 2 will usually be 0.01 to 3.0 mm and preferably 0.1 to 1.5 mm.

From the viewpoint of increasing the concealing property of the top sheet 2, an inorganic filler such as titanium oxide, barium sulfate or calcium carbonate may be added to the top sheet 2.

The top sheet 2 may also be a laminated film. Examples of laminated films include laminated films of a synthetic resin film layer and a fiber aggregate layer provided on the clothing side surface. Fiber aggregate layers include sheets or nonwoven fabrics of hydrophilic fiber aggregates, for example. A nonwoven fabric to be used as the fiber aggregate layer is preferably a tissue. A "tissue" is thin paper with a basis weight of at least 10 $g/m^2$ and no greater than 20 $g/m^2$, composed mainly of Kraft pulp or rayon for wet strength. The thickness of the fiber aggregate layer is preferably 0.1 to 0.5 mm. A fiber aggregate layer can also impart hydrophilicity and flexibility to the top sheet 2. Using a tissue for the fiber aggregate layer is also convenient as tissue sheets are less expensive than other sheets or nonwoven fabrics and are abundantly available on the market. While the strength of a tissue layer is low, its use together with a synthetic resin film layer will ensure strength for the top sheet 2.

As shown in FIG. 1 and FIG. 2, compressed grooves 5a, 5b are formed in each of the perimeters of the excretory opening contact region 20a and peripheral region 20b of the top sheet 2. Since the sanitary napkin 1 stably undergoes outward deformation starting from the compressed grooves 5a, 5b, extension of the extensible regions 21 which prevents excessive compression of the absorbent body 4, and elastic recoverability of the flexible regions 22 which prevents distortion of the top sheet 2, are effectively produced during outward deformation of the sanitary napkin 1.

The compressed grooves 5a, 5b are formed by compressing and integrating the perimeters of the excretory opening contact region 20a and peripheral region 20b, and the absorbent body 4 by, for example, embossing using a heating roller.

As shown in FIG. 1 and FIG. 2, the compressed grooves 5a, 5b are formed over the entire perimeters of excretory opening contact region 20a and peripheral region 20b. As an additional modification to this embodiment, the compressed grooves 5a, 5b may be formed over a portion of the perimeters of the excretory opening contact region 20a and peripheral region 20b.

As shown in FIG. 2, an adhesive layer S is provided between the absorbent body 4 and the back sheet 3, and the absorbent body 4 is anchored to the back sheet 3 by the adhesive layer S. The adhesive layer S is formed over roughly the entire bonding surfaces of the absorbent body 4 and back sheet 3, but as an additional modification to this embodiment, the adhesive layer S may be formed over portions of the bonding surfaces of the absorbent body 4 and back sheet.

Examples for the adhesive in the adhesive layer S include hot-melt adhesives, with examples of hot-melt adhesives including pressure-sensitive adhesives and heat-sensitive adhesives composed mainly of rubber-based compounds such as styrene-ethylene-butadiene-styrene (SEBS), styrene-butadiene-styrene (SBS) or styrene-isoprene-styrene (SIS), or composed mainly of olefin-based compounds such as linear low-density polyethylene; and water-sensitive adhesives comprising water-soluble polymers (such as polyvinyl alcohol, carboxylmethyl cellulose and gelatin) or water-swelling polymers (such as polyvinyl acetate and sodium polyacrylate). Specific examples of adhesive coating methods include spiral coating application, coater application, curtain coater application and summit-gun coating.

The perimeters of the excretory opening contact region 20a and the peripheral region 20b are anchored to the absorbent body 4 through the compressed grooves 5a, 5b, and the absorbent body 4 is anchored to the back sheet 3 through the adhesive layer S. That is, the perimeter of the excretory opening contact region 20a is anchored to the back sheet 3 through the compressed groove 5a and the adhesive layer S, while the perimeter of the peripheral region 20b is anchored to the back sheet 3 through the compressed groove 5b and the adhesive layer S. Consequently, separation of the excretory opening contact region 20a and peripheral region 20b with the back sheet 3 is prevented when the sanitary napkin 1 is deformed outward, and tension is effectively applied to the flexible regions 22, while extension of the extensible regions 21 which prevents excessive compression of the absorbent body 4, and elastic recoverability of the flexible regions 22 which prevents distortion of the top sheet 2, are effectively produced.

As shown in FIG. 2, the space between the top sheet 2 and the back sheet 3 is divided by the compressed grooves 5a, 5b, forming a space 6a closed by the compressed groove 5a and a space 6b closed by the compressed grooves 5a, 5b, between the top sheet 2 and the back sheet 3. The absorbent body 4 is divided into an absorbent body 4a present in the space 6a and an absorbent body 4b present in the space 6b, by the compressed grooves 5a, 5b. The absorbent body 4a causes the thickness of the excretory opening contact region 20a to already be protruding out, which can induce stabilized outward deformation of the excretory opening contact region 20a by the compressed grooves 5a, 5b, thus improving the fitting property of the excretory opening contact region 20a for the user. Since the absorbent body 4b has higher density than the absorbent body 4a, and easily maintains rigidity even after absorption of excreta, twisting of the sanitary napkin 1 as a whole after absorption of excreta is prevented.

The back sheet 3 is provided on the side in contact with the clothing (underwear) of the user, to prevent leakage of liquid excreta that has been absorbed in the absorbent body 4. The back sheet 3 is preferably moisture-permeable in addition to being liquid-impermeable, in order to reduce mustiness during wear.

The back sheet 3 is, for example, a waterproof treated nonwoven fabric, a film of a synthetic resin (such as polyethylene, polypropylene and polyethylene terephthalate), a composite sheet comprising a nonwoven fabric and a synthetic resin film (such as a composite film having an air permeable synthetic resin film bonded to a spunbond or spunlace nonwoven fabric), or an SMS nonwoven fabric comprising a highly water-resistant meltblown nonwoven fabric sandwiched between high-strength spunbond nonwoven fabrics.

The absorbent body 4 has an absorbent material layer. The absorbent material contained in the absorbent material layer is not particularly restricted so long as it can absorb liquid excreta of the user. The absorbent material may be, for example, water-absorbent fibers or a high-water-absorbing material (for example, a high-water-absorbent resin or high-water-absorbent fibers). The absorbent material layer may also include an antiblocking agent, ultraviolet absorber, thickening/branching agent, delustering agent, coloring agent, or different types of modifiers.

Examples of water-absorbent fibers include wood pulp obtained using a conifer or broadleaf tree material as the starting material (for example, mechanical pulp such as groundwood pulp, refiner ground pulp, thermomechanical pulp and chemithermomechanical pulp; chemical pulp such as Kraft pulp, sulfide pulp and alkaline pulp; and semichemical pulp); mercerized pulp or crosslinked pulp obtained by chemical treatment of wood pulp; nonwood pulp such as bagasse, kenaf, bamboo, hemp and cotton (for example, cotton linter); regenerated cellulose such as rayon and fibril rayon; and semi-synthetic celluloses such as acetates and triacetates, among which ground pulp is preferred from the viewpoint of low cost and easy shaping.

Examples of high-water-absorbing materials include starch-based, cellulose-based and synthetic polymer high-water-absorbing materials. Examples of starch-based or cellulose-based high-water-absorbing materials include starch-acrylic acid (salt) graft copolymer, saponified starch-acrylonitrile copolymer and crosslinked sodium carboxymethyl cellulose, and examples of synthetic polymer-based high-water-absorbing materials include polyacrylic acid salt-based, polysulfonic acid salt-based, maleic anhydride salt-based, polyacrylamide-based, polyvinyl alcohol-based, polyethylene oxide-based, polyaspartic acid salt-based, polyglutamic acid salt-based, polyalginic acid salt-based, starch-based and cellulose-based high water-absorbent resins (Superabsorbent Polymers: SAP), among which polyacrylic acid salt-based (especially sodium polyacrylate-based) high water-absorbent resins are preferred. Examples of high-water-absorbing material forms include particulate, filamentous and scaly forms, and in the case of particulates, the particle size is preferably 50 to 1000 μm and more preferably 100 to 600 μm.

The amount of highly absorbent material contained in the absorbent material layer may be appropriately changed according to the properties to be exhibited by the sanitary napkin 1 (for example, absorption properties and lightweight properties), but it will usually be 0 to 50 mass %, preferably 3 to 30 mass % and more preferably 5 to 15 mass % of the absorbent material layer.

The thickness, basis weight and density of the absorbent material layer may also be appropriately changed according to the properties to be exhibited by the sanitary napkin 1 (for example, absorption properties and lightweight properties). The thickness of the absorbent material layer will usually be 1 to 20 mm, preferably 2 to 15 mm and more preferably 2 to 10 mm, the basis weight will usually be 100 to 1000 $g/m^2$, preferably 150 to 700 $g/m^2$ and more preferably 200 to 500 $g/m^2$, and the density will usually be 0.005 to 0.5 $g/cm^2$, preferably 0.01 to 0.2 $g/cm^3$ and more preferably 0.01 to 0.1 $g/cm^3$. The thickness, basis weight and density of the absorbent material layer may vary before and after forming the compressed grooves 5a, 5b.

From the viewpoint of improving the cushioning properties of the absorbent body 4, the absorbent body 4 preferably has a cushion layer. The cushion layer may be formed, for example, on the surface on the top sheet 2 side or back sheet 3 side of the absorbent material layer, and preferably the surface on the top sheet 2 side, in which case the absorbent body 4 takes the form of a layered body with an absorbent material layer and a cushion layer.

The absorbent body 4 may be covered with a covering material. The covering material is not particularly restricted so long as it has liquid-permeable and absorbent body-holding properties, and from the viewpoint of low cost and absorbent body-holding properties, it is preferably a tissue composed mainly of ground pulp and formed by a wet method.

When the sanitary napkin 1 is inserted in the crotch of a user and folded at the excreta-receiving region 20 of the top sheet 2, being deformed outward toward the excreta-receiving region 20 side, it exhibits the following effect.

Figure 4:
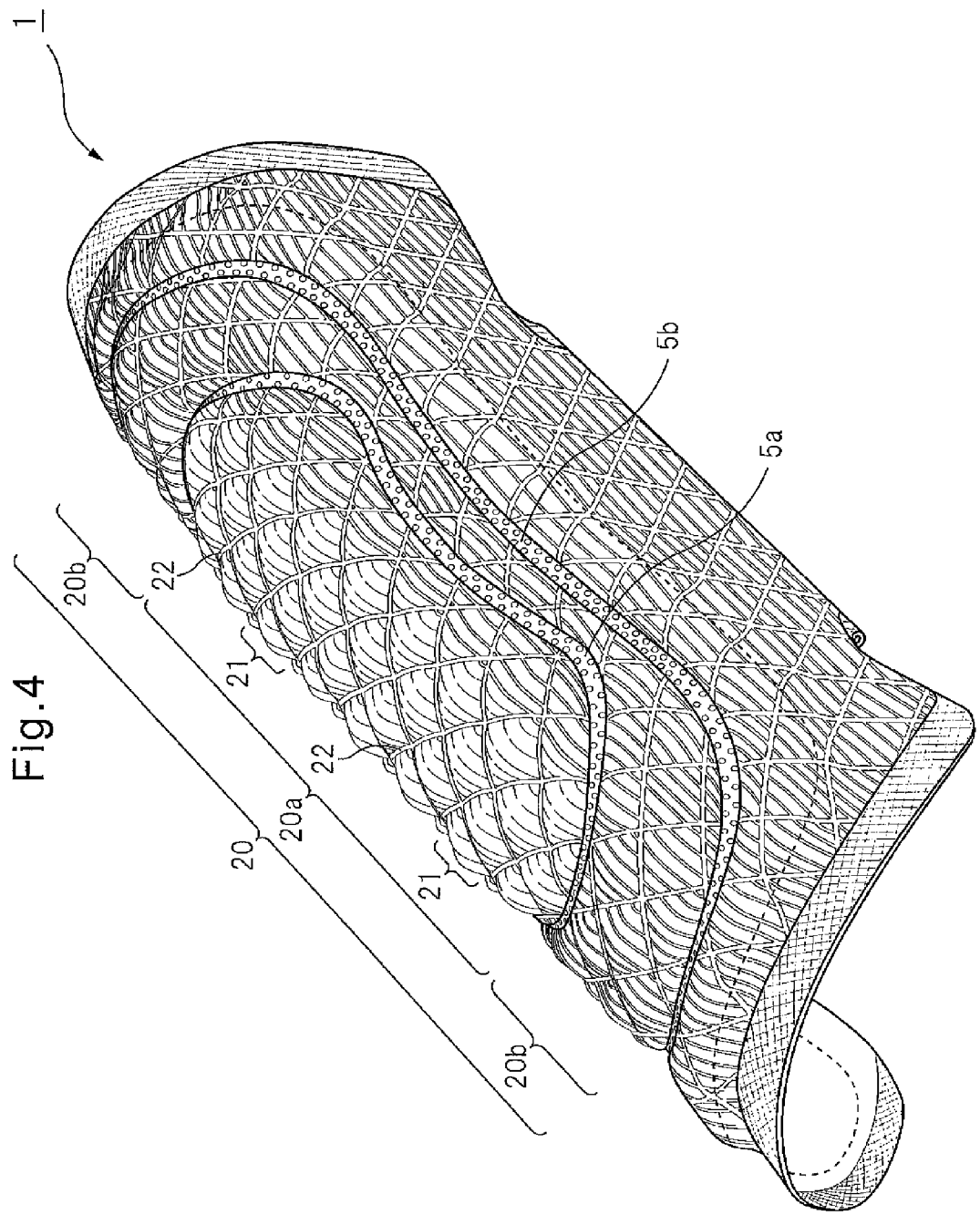
FIG. 4 is a perspective view of a sanitary napkin according to an embodiment of the invention, when it is deformed outward.

As shown in FIG. 4, when the sanitary napkin 1 is deformed outward, the top sheet 2 and back sheet 3 are deformed outward while sandwiching the absorbent body 4. When this occurs, since the extensible regions 21 in the liquid-receiving region 20 of the top sheet 2 are extendable in the widthwise direction of the sanitary napkin 1, the absorbent body 4 is not easily subjected to pressing force by the liquid-receiving region 20. Thus, excessive compression of the absorbent body 4 due to deformation of the sanitary napkin 1, and the consequent rewetting, are prevented.

Also, when the sanitary napkin 1 undergoes deformation while the folding angle is varied (for example, when the wearer of the sanitary napkin 1 changes posture causing the folding angle of the sanitary napkin 1 to become acute or obtuse), elastic recoverability (repulsion) of the flexible regions 22 causes the top sheet 2 to easily follow deformation of the sanitary napkin 1, thus preventing distortion of the top sheet 2 due to extension of the extensible regions 21, and sticking of the distorted sheet onto skin.

<Second Embodiment>

According to the second embodiment, a blood modifying agent is coated onto the surface of the top sheet 2 of the sanitary napkin 1. Menstrual blood that has been discharged onto the top sheet 2 has its viscosity and surface tension lowered by the blood modifying agent, and it therefore rapidly migrates from the top sheet 2 into the absorbent body 4 and is absorbed into the absorbent body 4. The increased absorption rate of menstrual blood into the absorbent body 4 helps prevent residue of highly viscous menstrual blood into the top sheet 2, reduces stickiness of the top sheet 2 and improves the surface drying property of the top sheet 2, while also leaving less of a visually unpleasant image for the wearer. Furthermore, leakage of menstrual blood that has been discharged onto the top sheet 2, from the widthwise direction side of the sanitary napkin 1, is also prevented.

The region coated with the blood modifying agent may be the entirety of the surface of the top sheet 2 or only a portion thereof, but preferably it includes at least the region contacting the excretory opening (vaginal opening) of the user. The blood modifying agent is preferably adhered to the top sheet 2 in the form of droplets or particulates, so that the liquid permeation holes of the top sheet 2 are not obstructed.

The coated basis weight of the blood modifying agent on the top sheet 2 is preferably 1 to 30 g/m$^2$ and more preferably 3 to 10 g/m$^2$. If the coating basis weight of the blood modifying agent is smaller than 1 g/m$^2$, it may be difficult to coat the blood modifying agent on the top sheet 2 in a stable manner, and if the coating basis weight of the blood modifying agent is greater than 30 g/m$^2$, the top sheet 2 may become greasy.

The method of coating the blood modifying agent may be, for example, a method of heating the blood modifying agent to a prescribed temperature, and then coating it using a contact coater such as a slot coater, or a non-contact coater such as a spray coater, curtain coater or spiral coater. A method of coating using a non-contact coater is preferred from the viewpoint of allowing the blood modifying agent to be evenly dispersed as droplets in the top sheet 2, and not incurring damage to the top sheet 2.

There are no particular restrictions on the time point at which the blood modifying agent is coated onto the top sheet 2, but from the viewpoint of limiting equipment investment, the blood modifying agent is preferably coated onto the top sheet 2 in the step of producing the sanitary napkin 1. When the blood modifying agent is to be coated onto the top sheet 2 in the step of producing the sanitary napkin 1, the blood modifying agent is preferably coated onto the top sheet 2 in a step near the final step, from the viewpoint of avoiding reduction in the blood modifying agent. For example, the top sheet 2 may be coated with the blood modifying agent just before the step of wrapping the sanitary napkin 1.

The region of the top sheet 2 that is to be coated with the blood modifying agent may also be coated with a hydrophilic agent, water-repellent agent or the like, or it may be rendered hydrophilic by corona treatment or plasma treatment. This will allow the hydrophilic areas and lipophilic areas to be mutually isolated in the blood modifying agent-coated region when the blood modifying agent is lipophilic, and both the hydrophilic components (mainly plasma) and lipophilic components (mainly blood cells) in menstrual blood will rapidly migrate from the top sheet 2 into the absorbent body 4.

The blood modifying agent will be described in detail in a separate section.

<Method for Producing Absorbent Article>

An embodiment of a method for producing an absorbent article will now be described, using a method for producing a sanitary napkin as an example.

Figure 5:
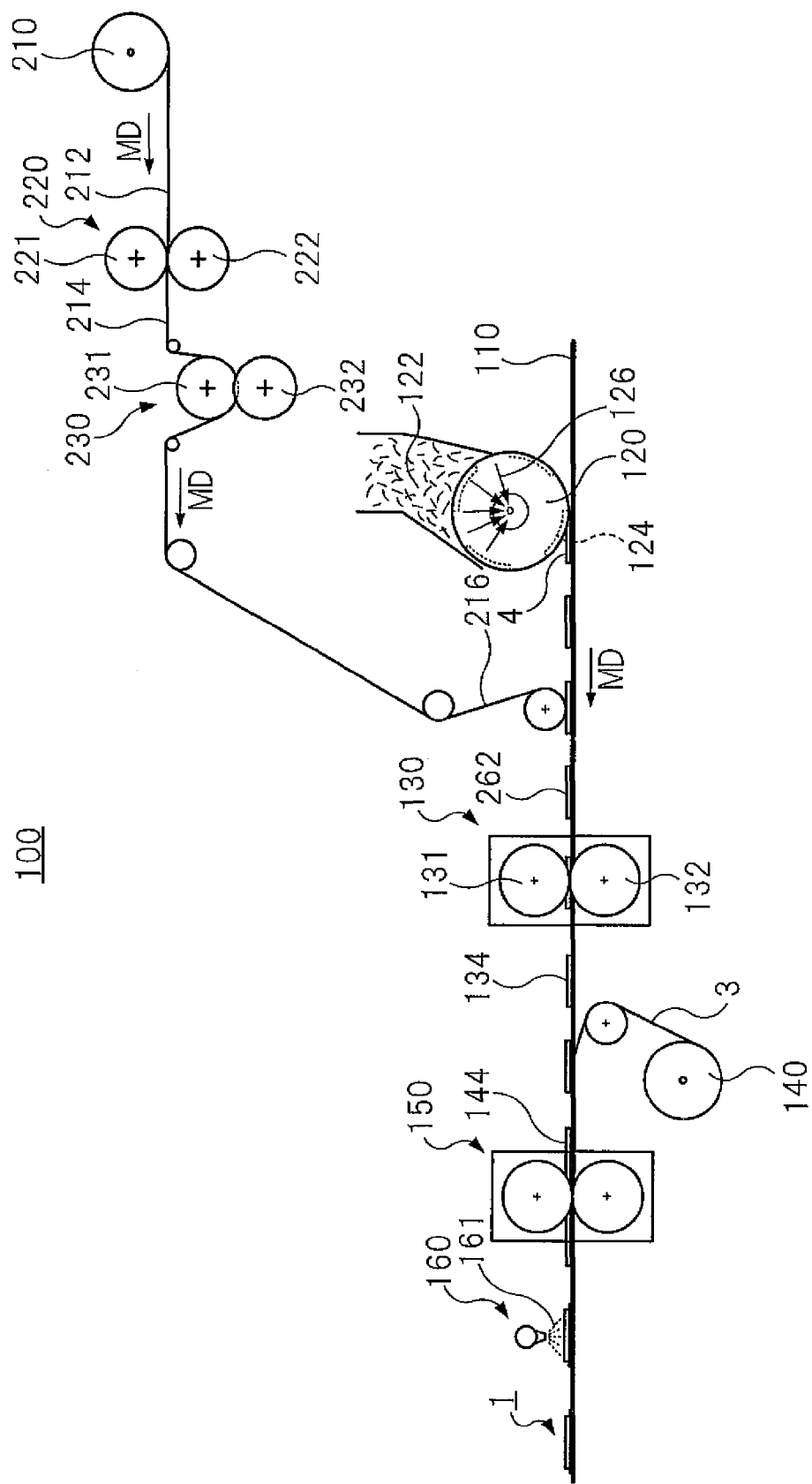
FIG. 5 is a diagram illustrating a method for producing a sanitary napkin according to an embodiment of the invention.

The production method according to this embodiment comprises a step of forming an absorbent body 4 (step 1A), a step of layering a top sheet 2 on an absorbent body 4 (step 2A), a step of forming compressed grooves in the layered body (step 3A), a step of layering a back sheet 3 (step 4A), a step of cutting out a sanitary napkin 1 (step 5A) and a step of coating the sanitary napkin 1 with a blood modifying agent (step 6A), and the production apparatus 100 shown in FIG. 5 is used.

[Step 1A]

Recesses 124 are formed at a prescribed pitch in the circumferential direction on the peripheral surface of a suction drum 120 rotating in the machine direction MD, as a molding form in which the absorbent body material 122 is to be packed. When the suction drum 120 is rotated and the recesses 124 approach the material feeder 121, the suction section 126 acts on the recesses 124 and the absorbent body material 122 supplied from the material feeder 121 is vacuum suctioned into the recesses 124. The material feeder 121 is formed to cover the suction drum 120, and the material feeder 121 supplies the absorbent body material 122 into the recesses 124 by air transport, forming an absorbent body 4 in the recesses 124. The absorbent body 4 formed in the recesses 124 is transferred onto a carrier sheet 110 advancing in the machine direction MD.

[Step 2A]

The top sheet 2 is layered on the absorbent body 4, forming a layered body 262. A method for producing the top sheet 2 will be described below.

[Step 3A]

The layered body 262 passes between the upper roll 131 and lower roll 132 of the embossing apparatus 130, forming compressed grooves in the layered body 262. Heights (not shown) with shapes corresponding to the compressed grooves are provided on the outer peripheral surface of the upper roll 131. The lower roll 132 is a plain roll having a smooth outer peripheral surface. When the layered body 262 passes between the upper roll 131 and lower roll 132 of the embossing apparatus 130, the layered body 262 becomes compressed in the thickness direction, and compressed grooves 5a, 5b are formed in the layered body 262. The compressed grooves 5a, 5b are formed, respectively, on the perimeters of the excretory opening contact region 20a and peripheral region 20b of the top sheet 2, and formation of the compressed grooves 5a, 5b causes the perimeters of the excretory opening contact region 20a and the peripheral region 20b to become integrated with the absorbent body 4.

[Step 4A]

The back sheet 3 supplied from the back sheet roll 140 is layered on the surface of the lower side of the layered body 134 on which the compressed grooves have been formed (the side opposite the top sheet), via an adhesive layer S, to form a continuous section 144 of the sanitary napkin 1.

[Step 5A]

A cutter 150 is used to cut the continuous section 144 of the sanitary napkin 1, thereby cutting out a sanitary napkin 1.

[Step 6A]

A blood modifying agent-coating spray 160 is used to coat the blood modifying agent 161 onto the center region of the sanitary napkin 1, forming a blood modifying agent layer on the surface of the top sheet 2.

The blood modifying agent layer is preferably formed in at least the excretory opening contact region 20a in the excreta-receiving region 20 of the top sheet 2.

For this embodiment, the blood modifying agent was coated after cutting out the sanitary napkin 1, but it may instead be coated at any stage before cutting, or it may be coated during the production steps for the top sheet 2, described below. In order to prevent dripping down of the blood modifying agent that has been coated during production, the blood modifying agent is preferably coated at a downstream stage of the production process, such as immediately before packaging of the sanitary napkin 1.

The method for producing the sanitary napkin 1 comprises, in addition to steps 1A to 6A, also a step of forming seal sections 7a, 7b, 8a, 8b and a step of forming pressure-sensitive adhesive sections 9a, 9b, 9c.

<Method for Producing Liquid-Permeable Sheet>

A working embodiment of a method for producing a liquid-permeable sheet according to the invention will now be described, as an example of a method for producing the top sheet 2 of a sanitary napkin 1.

The production method according to this embodiment comprises a step (1B) of forming recesses in a synthetic resin film sheet and a step (2B) of gear stretching the synthetic resin film sheet.

[Step 1B]

Figure 7:
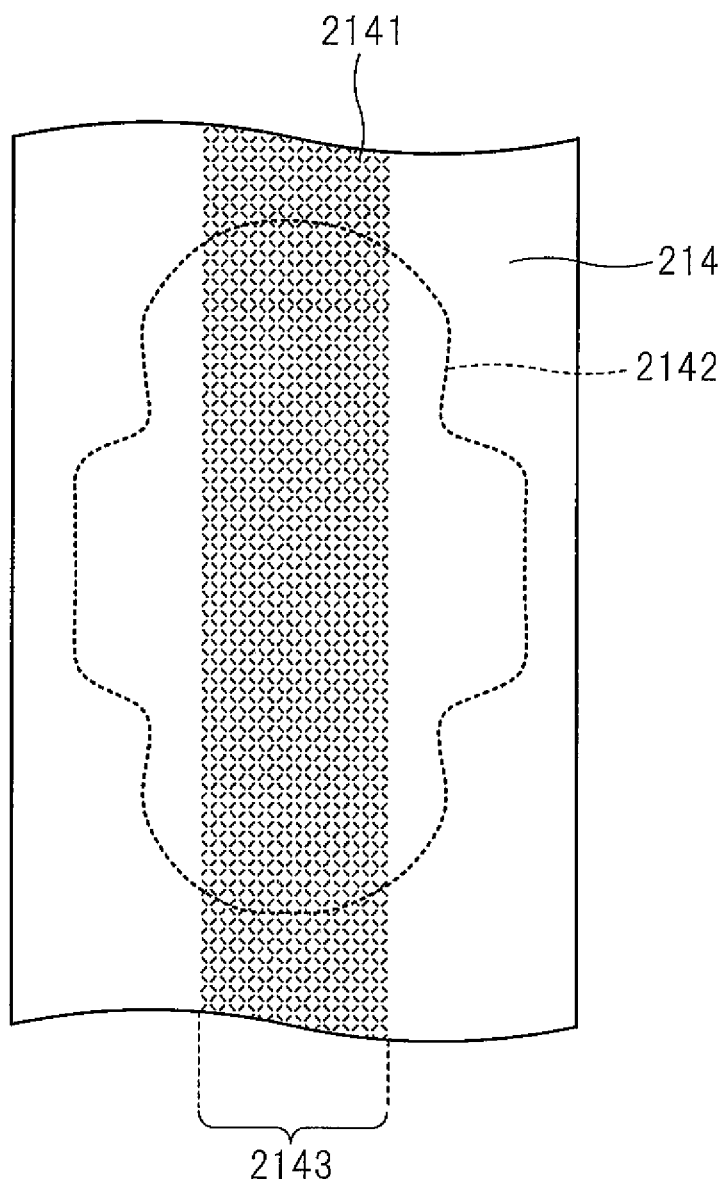
FIG. 7 is a diagram illustrating the region of a top sheet in which recesses are formed by a recess-forming roll.

As shown in FIG. 5, the synthetic resin film sheet 212 supplied from a roll 210 passes through a recess-forming roll 220 and recesses 2141 are formed in the synthetic resin film sheet 212 (see FIG. 7). The recess-forming roll 220 comprises a roulette roll 221 and a preheated roll 222 with a smooth surface.

FIGS. 6(a) and (b) show examples of the roulette roll 221. FIG. 6(a) shows the entire roulette roll 221, and FIG. 6(b) is a magnified view of section 223 having concavoconvexities on the outer peripheral surface of the roulette roll 221. FIG. 6(c) shows an example of the preheated roll 222 which has a smooth surface. Lattice-like heights 224 are formed on the surface 223 of the roulette roll 221. As a result, rhomboid recesses 225 are formed in the surface of the roulette roll 221. The shapes of the recesses 225 of the roulette roll 221 are not limited to being rhomboid, and may instead be square, rectangular, parallelogram-shaped, trapezoid, triangular, hexagonal, or the like.

The center line spacing between the heights 224 arranged parallel on the lattice-like heights 224, i.e. the pitch of the lattice-like heights 224, is usually preferred to be 0.2 to 10 mm, and more preferably 0.4 to 2 mm. The widths of the lattice-like heights 224 are preferably 0.01 to 1 mm and more preferably 0.03 to 0.1 mm. The lengths of the sides of the rhomboid recesses 225 are preferably 0.1 to 5 mm and more preferably 0.2 to 1 mm. These ranges are preferred from the viewpoint of improving formability of the recesses in the synthetic resin film sheet.

The preheated roll 222 with a smooth surface is kept at a temperature between 70° C. and 100° C., and it heats the supplied synthetic resin film sheet 212. This softens the synthetic resin film sheet 212 and facilitates formation.

When the synthetic resin film sheet 212 passes between the rolls 221 and 222, the synthetic resin film sheet 212 receives strong pressure in the thickness direction at the sections in contact with the lattice-like heights 224. This causes thin recesses 2141 to form in the synthetic resin film sheet 214, as shown in FIG. 7. The recesses 2141 formed in the synthetic resin film sheet 214 are actually smaller than shown in FIG. 7, and the number of recesses 2141 per unit area is greater than shown in FIG. 8. The recesses 2141 are formed in the region 2143 of the synthetic resin film sheet 214 corresponding to the center region of the sanitary napkin 1. The region of the synthetic resin film sheet 214 corresponding to the sanitary napkin 1 is the region indicated by the dotted line labeled 2142.

[Step 2B]

By passing the recess-formed synthetic resin film sheet 214 through the stretching gear roll 230, the regions of the synthetic resin film sheet 214 corresponding to the extensible regions 21 of the top sheet 2 become folded, producing a synthetic resin film sheet 216 in which bellows structures 210 are formed. The bellows structures 210 in the synthetic resin film sheet 216 are laid out in the machine direction (MD) and aligned in the widthwise direction, the cross-sectional shapes along the widthwise direction being wavy with a combination of roughly U-shaped curves. The bellows structures 210 extending in the machine direction are interrupted at multiple locations in the synthetic resin film sheet 216. That is, the bellows structures 210 are formed in a discontinuous manner in the synthetic resin film sheet 216, the synthetic resin film sheet 214 being not folded at the discontinuous sections. The discontinuous sections correspond to the flexible regions 22 of the top sheet 2.

The stretching gear roll 230 comprises an upper roll 231 and a lower roll 232. FIG. 8(a) is a diagram illustrating the upper roll 231 of the stretching gear roll 230, FIG. 8(b) is a diagram illustrating the gear teeth 233 situated on the peripheral surface of the upper roll 231, and FIG. 8(c) is a cross-sectional view of FIG. 8(b) along line B-B. The gear teeth 233 extend in a discontinuous manner in the circumferential direction of the upper roll 231. That is, the gear teeth 233 extending in the circumferential direction of the upper roll 231 are interrupted at multiple locations along them. The locations 234 where the gear teeth 233 are interrupted result in formation of discontinuous sections corresponding to the flexible regions 22 of the top sheet 2. The locations 234 where the gear teeth 233 are interrupted are disposed along a straight line in a direction diagonal to the direction in which the gear teeth 233 extend.

The widths of the gear teeth 233 are 0.3 mm to 0.5 mm, for example, and the distance between the centers of the adjacent gear teeth 233 are 1.0 to 1.2 mm, for example.

FIG. 9(a) is a diagram showing the lower roll 232 of the stretching gear roll 230, FIG. 9(b) is a diagram showing the gear teeth 235 situated on the peripheral surface of the lower roll 232, and FIG. 9(c) is a cross-sectional view of FIG. 9(b) along line C-C. The gear teeth 235 extend in the circumferential direction of the lower roll 232. The lower roll 232, unlike the upper roll 231, is not interrupted at multiple locations along it. The widths of the gear teeth 235 may be equal to the widths of the gear teeth 233 of the upper roll 231, for example, and the distance between the centers of adjacent gear teeth 235 may be equal to the distance between the centers of the gear teeth 233 of the upper roll 231, for example.

The length of the upper roll 231 in the radial direction at the section where the gear teeth 233 of the upper roll 231 engage with the gear teeth 235 of the lower roll 232, i.e. the mesh depth, is 1.25 mm, for example. The gaps between the gear teeth 233 of the upper roll 231 and the gear teeth 235 of the lower roll 232, when the gear teeth 233 of the upper roll 231 and the gear teeth 235 of the lower roll 232 have been meshed, are 0.25 to 0.45 mm, for example.

When the synthetic resin film sheet 214 passes through the stretching gear roll 230, openings are formed in the region 2143 of the synthetic resin film sheet 214 in which the recesses 2141 have been formed (see FIG. 7), corresponding to the liquid permeation holes 26 of the top sheet 2 (see FIG. 3).

Figure 10:
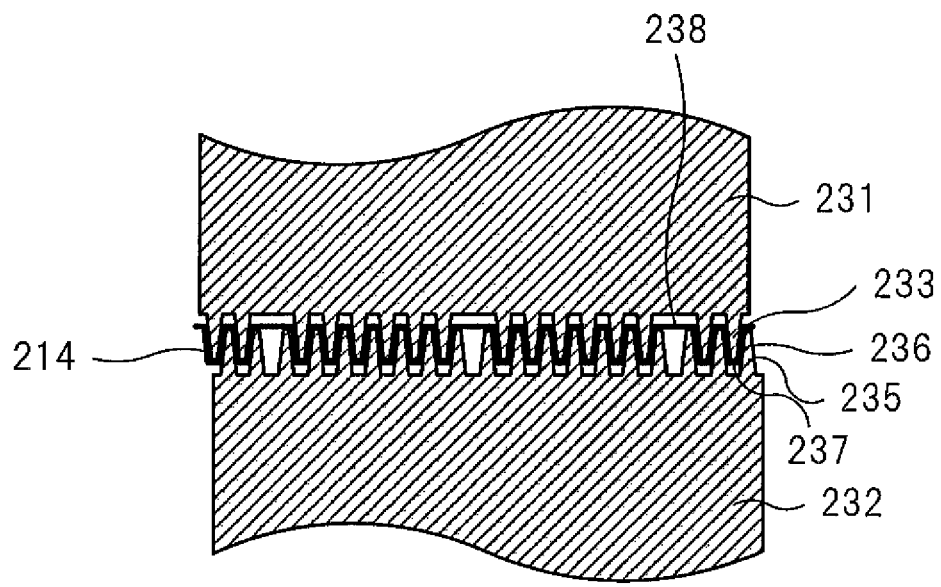
FIG. 10 is an illustration of a top sheet stretched by a stretching gear roll.

The principle by which openings are formed in the synthetic resin film sheet 214 after the synthetic resin film sheet 214 has passed through the stretching gear roll 230 will now be explained with reference to FIG. 10. The explanation of this principle is not intended to limit the scope of the invention.

The synthetic resin film sheet 214 is stretched to a large degree at the sections 236 where the gear teeth 233 of the upper roll 231 and the gear teeth 235 of the lower roll 232 are meshed. Since the synthetic resin film sheet 214 is thinner at the sections in which the recesses 2141 (see FIG. 7) have been formed in the recess-forming step, and they are also the sections that have been damaged by the lattice-like heights 224 of the roulette roll 221, their strength is weak and the recesses 2141 of the synthetic resin film sheet 214 tear when subjected to stretching. As a result, the recesses 2141 of the synthetic resin film sheet 214 tear at the sections 236 of the synthetic resin film sheet 214 that have been stretched, such that the torn sections of the synthetic resin film sheet 214 widen, forming openings.

The synthetic resin film sheet 214 is not significantly stretched at the sections 237, 238 where the gear teeth 233 of the upper roll 231 and the gear teeth 235 of the lower roll 232 are not meshed. Consequently, even when the synthetic resin film sheet 214 passes through the stretching gear roll 230, the recesses 2141 formed in the recess-forming step are not torn and do not become openings at the sections 237, 238 of the synthetic resin film sheet 214 where the gear teeth 233 of the upper roll 231 and the gear teeth 235 of the lower roll 232 are not meshed.

In the regions of the synthetic resin film sheet 214 where no recesses 2141 have been formed, the synthetic resin film sheet 214 is not torn, and therefore no openings are formed, at the section 236 where the gear teeth 233 of the upper roll 231 and the gear teeth 235 of the lower roll 232 are meshed, even when the synthetic resin film sheet 214 is stretched to a high degree.

<Blood Modifying Agent>

The blood modifying agent of the present invention has an IOB of about 0.00-0.60, a melting point of about 45° C. or less, and a water solubility of about 0.00-0.05 g in 100 g of water at 25° C.

The IOB (Inorganic Organic Balance) is an indicator of the hydrophilic-lipophilic balance, and as used herein, it is the value calculated by the following formula by Oda et al.:

IOB=inorganic value/organic value.

The inorganic value and the organic value are based on the organic paradigm described in "Organic compound predictions and organic paradigms" by Fujita A., Kagaku no Ryoiki (Journal of Japanese Chemistry), Vol. 11, No. 10 (1957) p. 719-725.

The organic values and inorganic values of major groups, according to Fujita, are summarized in Table 1 below.

TABLE 1

| Group | Inorganic value | Organic value |
| --- | --- | --- |
| —COOH | 150 | 0 |
| —OH | 100 | 0 |
| —O—CO—O— | 80 | 0 |
| —CO— | 65 | 0 |
| —COOR | 60 | 0 |
| —O— | 20 | 0 |

TABLE 1-continued

| Group | Inorganic value | Organic value |
| --- | --- | --- |
| Triple bond | 3 | 0 |
| Double bond | 2 | 0 |
| $CH_2$ | 0 | 20 |
| iso-branch | 0 | −10 |
| tert-branch | 0 | −20 |
| Light metal (salt) | ≥500 | 0 |
| Heavy metal (salt), amine, $NH_3$ salt | ≥400 | 0 |

For example, in the case of an ester of tetradecanoic acid which has 14 carbon atoms and dodecyl alcohol which has 12 carbon atoms, the organic value is 520 ($CH_2$, 20×26) and the inorganic value is 60 (—COOR, 60×1), and therefore IOB=0.12.

In the blood modifying agent, the IOB is about 0.00-0.60, preferably about 0.00-0.50, more preferably about 0.00-0.40 and even more preferably about 0.00-0.30. This is because a lower IOB is associated with higher organicity and higher affinity with blood cells.

As used herein, the term "melting point" refers to the peak top temperature for the endothermic peak during conversion from solid to liquid, upon measurement with a differential scanning calorimetry analyzer at a temperature-elevating rate of 10° C./min. The melting point may be measured using a Model DSC-60 DSC measuring apparatus by Shimadzu Corp., for example.

If the blood modifying agent has a melting point of about 45° C. or less, it may be either liquid or solid at room temperature, or in other words, the melting point may be either about 25° C. or higher or below about 25° C., and for example, it may have a melting point of about −5° C. or about −20° C. The reason why the blood modifying agent should have a melting point of about 45° C. or less will be explained below.

The blood modifying agent does not have a lower limit for the melting point, but the vapor pressure is preferably low. The vapor pressure of the blood modifying agent is preferably about 0-200 Pa, more preferably about 0-100 Pa, even more preferably about 0-10 Pa, even more preferably about 0-1 Pa, and even more preferably about 0.0-0.1 Pa at 25° C. (1 atmosphere). Considering that the absorbent article is to be used in contact with the human body, the vapor pressure is preferably about 0-700 Pa, more preferably about 0-100 Pa, even more preferably about 0-10 Pa, even more preferably about 0-1 Pa, and even more preferably 0.0-0.1 Pa, at 40° C. (1 atmosphere). If the vapor pressure is high, gasification may occur during storage and the amount of blood modifying agent may be reduced, and as a consequence problems, such as odor during wear, may be created.

The melting point of the blood modifying agent may also differ depending on the weather or duration of wear. For example, in regions with a mean atmospheric temperature of about 10° C. or less, using a blood modifying agent with a melting point of about 10° C. or less may allow the blood modifying agent to stably modify blood after excretion of menstrual blood, even if it has been cooled by the ambient temperature.

Also, when the absorbent article is used for a prolonged period of time, the melting point of the blood modifying agent is preferably at the high end of the range of about 45° C. or less. This is because the blood modifying agent is not easily affected by sweat or friction during wearing, and will not easily migrate even during prolonged wearing.

A water solubility of 0.00-0.05 g can be confirmed by adding 0.05 g of sample to 100 g of deionized water at 25° C., allowing the mixture to stand for 24 hours, and gently stirring after 24 hours if necessary and then visually evaluating whether or not the sample has dissolved.

The term "solubility" used herein in regard to water solubility includes cases where the sample completely dissolves in deionized water to form a homogeneous mixture, and cases where the sample is completely emulsified. Here, "completely" means that no mass of the sample remains in the deionized water.

In the art, top sheet surfaces are coated with surfactants in order to alter the surface tension of blood and promote rapid absorption of blood. However, because surfactants generally have high water solubility, the surfactant-coated top sheet is highly miscible with hydrophilic components (such as, blood plasma) in the blood and therefore, instead, they tend to cause residue of blood on the top sheet. The aforementioned blood modifying agent has low water solubility and therefore, unlike conventionally known surfactants, it does not cause residue of blood on the top sheet and allows rapid migration into the absorbent body.

As used herein, a water solubility in 100 g of water at 25° C. may be simply referred to as "water solubility".

As used herein, "weight-average molecular weight" includes the concept of a polydisperse compound (for example, a compound produced by stepwise polymerization, an ester formed from a plurality of fatty acids and a plurality of aliphatic monohydric alcohols), and a simple compound (for example, an ester formed from one fatty acid and one aliphatic monohydric alcohol), and in a system comprising $N_i$ molecules with molecular weight $M_i$ (i =1, or i=1, 2 . . . ), it refers to $M_w$ determined by the following formula.

$$M_w = \Sigma N_i M_i^2 / \Sigma N_i M_i$$

As used herein, the weight-average molecular weights are the values measured by gel permeation chromatography (GPC), based on polystyrene.

The GPC measuring conditions may be the following, for example.

Device: Lachrom Elite high-speed liquid chromatogram by Hitachi High-Technologies Corp.

Columns: SHODEX KF-801, KF-803 and KF-804, by Showa Denko K.K.

Eluent: THF
Flow rate: 1.0 mL/min
Driving volume: 100 μL
Detection: RI (differential refractometer)

The weight-average molecular weights listed in the examples of the present specification were measured under the conditions described below.

Preferably, the blood modifying agent is selected from the group consisting of following items (i)-(iii), and combinations thereof:

(i) a hydrocarbon;
(ii) a compound having (ii-1) a hydrocarbon moiety, and (ii-2) one or more, same or different groups selected from the group consisting of carbonyl group (—CO—) and oxy group (—O—) inserted between a C—C single bond of the hydrocarbon moiety; and
(iii) a compound having (iii-1) a hydrocarbon moiety, (iii-2) one or more, same or different groups selected from the group consisting of carbonyl group (—CO—) and oxy group (—O—) inserted between a C—C single bond of the hydrocarbon moiety, and (iii-3) one or more, same or different groups selected from the group consisting of carboxyl group (—COOH) and hydroxyl group (—OH) substituted for a hydrogen of the hydrocarbon moiety.

As used herein, "hydrocarbon" refers to a compound composed of carbon and hydrogen, and it may be a chain hydrocarbon, such as a paraffinic hydrocarbon (containing no double bond or triple bond, also referred to as alkane), an olefin-based hydrocarbon (containing one double bond, also referred to as alkene), an acetylene-based hydrocarbon (containing one triple bond, also referred to as alkyne), or a hydrocarbon comprising two or more bonds selected from the group consisting of double bonds and triple bonds, and cyclic hydrocarbon, such as aromatic hydrocarbons and alicyclic hydrocarbons.

Preferred as such hydrocarbons are chain hydrocarbons and alicyclic hydrocarbons, with chain hydrocarbons being more preferred, paraffinic hydrocarbons, olefin-based hydrocarbons and hydrocarbons with two or more double bonds (containing no triple bond) being more preferred, and paraffinic hydrocarbons being even more preferred.

Chain hydrocarbons include linear hydrocarbons and branched hydrocarbons.

When two or more oxy groups (—O—) are inserted in the compounds of (ii) and (iii) above, the oxy groups (—O—) are not adjacent each other. Thus, compounds (ii) and (iii) do not include compounds with continuous oxy groups (i.e., peroxides).

In the compounds of (iii), compounds in which at least one hydrogen on the hydrocarbon moiety is substituted with a hydroxyl group (—OH) are preferred over compounds in which at least one hydrogen on the hydrocarbon moiety is substituted with a carboxyl group (—COOH). As shown in Table 1, the carboxyl groups bond with metals and the like in menstrual blood, drastically increasing the inorganic value from 150 to 400 or greater, and therefore a blood modifying agent with carboxyl groups can increase the IOB value to more than about 0.60 during use, potentially lowering the affinity with blood cells.

More preferably, the blood modifying agent is selected from the group consisting of following items (i')-(iii'), and combinations thereof:

(i') a hydrocarbon;
(ii') a compound having (ii'-1) a hydrocarbon moiety, and (ii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety; and
(iii') a compound having (iii'-1) a hydrocarbon moiety, (iii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety, and (iii'-3) one or more, same or different groups selected from the group consisting of carboxyl group (—COOH) and hydroxyl group (—OH) substituted for a hydrogen on the hydrocarbon moiety.

When 2 or more same or different bonds are inserted in the compound of (ii') or (iii'), i.e., when 2 or more same or different bonds selected from the group consisting carbonyl bonds (—CO—), ester bonds (—COO—), carbonate bonds (—OCOO—) and ether bonds (—O—) are inserted, the bonds are not adjacent to each other, and at least one carbon atom lies between each of the bonds.

The blood modifying agent is more preferably a compound with no more than about 1.8 carbonyl bonds (—CO—), no more than 2 ester bonds (—COO—), no more than about 1.5 carbonate bonds (—OCOO—), no more than about 6 ether bonds (—O—), no more than about 0.8 carboxyl groups (—COOH) and/or no more than about 1.2 hydroxyl groups (—OH), per 10 carbon atoms in the hydrocarbon moiety.

Even more preferably, the blood modifying agent is selected from the group consisting of following items (A)-(F), and combinations thereof:

(A) an ester of (A1) a compound having a chain hydrocarbon moiety and 2-4 hydroxyl groups substituted for hydrogens on the chain hydrocarbon moiety, and (A2) a compound having a chain hydrocarbon moiety and 1 carboxyl group substituted for a hydrogen on the chain hydrocarbon moiety;

(B) an ether of (B1) a compound having a chain hydrocarbon moiety and 2-4 hydroxyl groups substituted for hydrogens on the chain hydrocarbon moiety, and (B2) a compound having a chain hydrocarbon moiety and 1 hydroxyl group substituted for a hydrogen on the chain hydrocarbon moiety;

(C) an ester of (C1) a carboxylic acid, hydroxy acid, alkoxy acid or oxoacid comprising a chain hydrocarbon moiety and 2-4 carboxyl groups substituted for hydrogens on the chain hydrocarbon moiety, and (C2) a compound having a chain hydrocarbon moiety and 1 hydroxyl group substituted for a hydrogen on the chain hydrocarbon moiety;

(D) a compound having a chain hydrocarbon moiety and one bond selected from the group consisting of ether bonds (—O—), carbonyl bonds (—CO—), ester bonds (—COO—) and carbonate bonds (—OCOO—) inserted between a C—C single bond of the chain hydrocarbon moiety;

(E) a polyoxy $C_2$-$C_6$$C_{2-6}$ alkylene glycol, or its ester or ether; and (F) a chain hydrocarbon.

The blood modifying agent in accordance with (A) to (F) will now be described in detail.

[(A) Ester of (A1) a Compound Having a Chain Hydrocarbon Moiety and 2-4 Hydroxyl Groups Substituted for Hydrogens on the Chain Hydrocarbon Moiety, and (A2) a Compound Having a Chain Hydrocarbon Moiety and 1 Carboxyl Group Substituted for a Hydrogen on the Chain Hydrocarbon Moiety]

In the (A) ester of (A1) a compound having a chain hydrocarbon moiety and 2-4 hydroxyl groups substituted for hydrogens on the chain hydrocarbon moiety, and (A2) a compound having a chain hydrocarbon moiety and 1 carboxyl group substituted for a hydrogen on the chain hydrocarbon moiety (hereunder also referred to as "compound (A)"), it is not necessary for all of the hydroxyl groups to be esterified so long as the IOB, melting point and water solubility are within the aforementioned ranges.

Examples of (A1) a compound having a chain hydrocarbon moiety and 2-4 hydroxyl groups substituted for hydrogens on the chain hydrocarbon moiety (hereunder also referred to as "compound (A1)") include chain hydrocarbon tetraols, such as alkanetetraols, including pentaerythritol, chain hydrocarbon triols, such as alkanetriols, including glycerins, and chain hydrocarbon diols, such as alkanediols, including glycols.

Examples of (A2) a compound having a chain hydrocarbon moiety and 1 carboxyl group substituted for a hydrogen on the chain hydrocarbon moiety (hereunder also referred to as "compound (A2)") include compounds in which one hydrogen on the hydrocarbon is substituted with one carboxyl group (—COOH), such as fatty acids.

Examples for compound (A) include (a₁) an ester of a chain hydrocarbon tetraol and at least one fatty acid, (a₂) an ester of a chain hydrocarbon triol and at least one fatty acid, and (a₃) an ester of a chain hydrocarbon diol and at least one fatty acids.

[(a₁) Esters of a Chain Hydrocarbon Tetraol and at Least One Fatty Acid]

Examples of an ester of a chain hydrocarbon tetraol and at least one fatty acid include tetraesters of pentaerythritol and fatty acids, represented by the following formula (1):

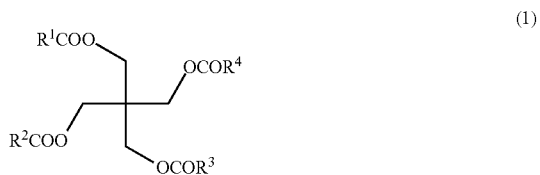

triesters of pentaerythritol and fatty acids, represented by the following formula (2):

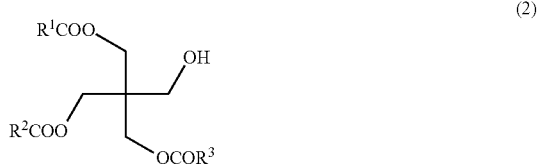

diesters of pentaerythritol and fatty acids, represented by the following formula (3):

and monoesters of pentaerythritol and fatty acids, represented by the following formula (4).

In the formulas, $R^1$-$R^4$ each represent a chain hydrocarbon.

The fatty acids consisting of the esters of pentaerythritol and fatty acids ($R^1COOH$, $R^2COOH$, $R^3COOH$, and $R^4COOH$) are not particularly restricted so long as the pentaerythritol and fatty acid esters satisfy the conditions for the IOH, melting point and water solubility, and for example, there may be mentioned saturated fatty acids, such as a $C_2$-$C_{30}$ saturated fatty acids, including acetic acid ($C_2$) ($C_2$ representing the number of carbons, corresponding to the number of carbons of each of $R^1C$, $R^2C$, $R^3C$ or $R^4C$, same hereunder), propanoic acid ($C_3$), butanoic acid ($C_4$) and its isomers, such as 2-methylpropanoic acid ($C_4$), pentanoic acid ($C_5$) and its isomers, such as 2-methylbutanoic acid ($C_5$) and 2,2-dimethylpropanoic acid ($C_5$), hexanoic acid ($C_6$), heptanoic acid ($C_7$), octanoic acid ($C_8$) and its isomers, such as 2-ethylhexanoic acid ($C_8$), nonanoic acid ($C_9$), decanoic acid ($C_{10}$), dodecanoic acid ($C_{12}$), tetradecanoic acid ($C_{14}$), hexadecanoic acid ($C_{16}$), heptadecanoic acid ($C_{17}$), octadecanoic acid ($C_{18}$), eicosanoic acid ($C_{20}$), docosanoic acid ($C_{22}$), tetracosanoic acid ($C_{24}$), hexacosanoic acid (C26), octacosanoic acid ($C_{28}$), triacontanoic acid ($C_{30}$), as well as isomers of the foregoing (excluding those mentioned above).

The fatty acid may also be an unsaturated fatty acid. Examples of unsaturated fatty acids include $C_3$-$C_{20}$ unsaturated fatty acids, such as monounsaturated fatty acids including crotonic acid ($C_4$), myristoleic acid (C14), palmitoleic acid ($C_{16}$), oleic acid ($C_{18}$), elaidic acid ($C_{18}$), vaccenic acid ($C_{18}$), gadoleic acid ($C_{20}$) and eicosenoic acid ($C_{20}$), di-unsaturated fatty acids including linolic acid ($C_{18}$) and eicosadienoic acid ($C_{20}$), tri-unsaturated fatty acids including linolenic acids, such as α-linolenic acid ($C_{18}$) and γ-linolenic acid ($C_{18}$), pinolenic acid ($C_{18}$), eleostearic acids, such as α-eleostearic acid ($C_{18}$) and β-eleostearic acid ($C_{18}$), Mead acid ($C_{20}$), dihomo-γ-linolenic acid ($C_{20}$) and eicosatrienoic acid ($C_{20}$), tetra-unsaturated fatty acids including stearidonic acid ($C_{20}$), arachidonic acid ($C_{20}$) and eicosatetraenoic acid ($C_{20}$), penta-unsaturated fatty acids including bosseopentaenoic acid ($C_{18}$) and eicosapentaenoic acid ($C_{20}$), and partial hydrogen adducts of the foregoing.

Considering the potential for degradation by oxidation and the like, the ester of pentaerythritol and a fatty acid is preferably an ester of pentaerythritol and a fatty acid, which is derived from a saturated fatty acid, i.e., an ester of pentaerythritol and a saturated fatty acid.

Also, in order to lower the IOB and result in greater hydrophobicity, the ester of pentaerythritol and a fatty acid is preferably a diester, triester or tetraester, more preferably a triester or tetraester, and even more preferably a tetraester.

In a tetraester of pentaerythritol and a fatty acid, the IOB is 0.60 if the total number of carbons of the fatty acid consisting of the tetraester of the pentaerythritol and fatty acid, i.e., the total number of carbons of the $R^1C$, $R^2C$, $R^3C$ and $R^4C$ portions in formula (1), is 15. Thus, when the total number of carbons of the fatty acid consisting of the tetraester of the pentaerythritol and fatty acid is approximately 15 or greater, the IOB satisfies the condition of being within about 0.00 to 0.60.

Examples of tetraesters of pentaerythritol and fatty acids include tetraesters of pentaerythritol with hexanoic acid ($C_6$), heptanoic acid ($C_7$), octanoic acid ($C_8$), such as 2-ethylhexanoic acid ($C_8$), nonanoic acid ($C_9$), decanoic acid ($C_{10}$) and/or dodecanoic acid ($C_{12}$).

In a triester of pentaerythritol and a fatty acid, the IOB is 0.58 if the total number of carbons of the fatty acid consisting of the triester of the pentaerythritol and fatty acid, i.e., the total number of carbons of the $R^1C$, $R^2C$ and $R^3C$ portions in formula (2), is 19. Thus, when the total number of carbons of the fatty acid consisting of the triester of the pentaerythritol and fatty acid is approximately 19 or greater, the IOB satisfies the condition of being within about 0.00 to 0.60.

In a diester of pentaerythritol and a fatty acid, the IOB is 0.59 if the total number of carbons of the fatty acid consisting of the diester of the pentaerythritol and fatty acid, i.e., the total number of carbons of the $R^1C$ and $R^2C$ portion in formula (3), is 22. Thus, when the total number of carbons of the fatty acid consisting of the diester of the pentaerythritol and fatty acid is approximately 22 or greater, the IOB satisfies the condition of being within about 0.00 to 0.60.

In a monoester of pentaerythritol and a fatty acid, the IOB is 0.60 if the total number of carbons of the fatty acid consisting of the monoester of the pentaerythritol and fatty acid, i.e. the total number of carbons of the $R^1C$ portion in formula (4), is 25. Thus, when the number of carbons of the fatty acid consisting of the monoester of the pentaerythritol and fatty acid is approximately 25 or greater, the IOB satisfies the condition of being within about 0.00 to 0.60.

The effects of double bonds, triple bonds, iso-branches and tert-branches are not considered in this calculation.

Commercial products which are esters of pentaerythritol and fatty acids include UNISTAR H-408BRS and H-2408BRS-22 (mixed product) (both products of NOF Corp.).

[($a_2$) Ester of a Chain Hydrocarbon Triol and at Least One Fatty Acid]

Examples of esters of a chain hydrocarbon triol and at least one fatty acid include triesters of glycerin and fatty acids, represented by formula (5):

diesters of glycerin and fatty acids, represented by the following formula (6):

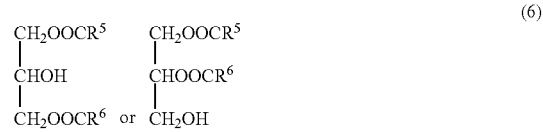

and monoesters of glycerin and fatty acids, represented by the following formula (7):

wherein $R^5$-$R^7$ each represent a chain hydrocarbon.

The fatty acid consisting of the ester of glycerin and a fatty acid ($R^5COOH$, $R^6COOH$ and $R^7COOH$) is not particularly restricted so long as the ester of glycerin and a fatty acid satisfies the conditions for the IOB, melting point and water solubility, and for example, there may be mentioned the fatty acids mentioned for the "($a_1$) Ester of a chain hydrocarbon tetraol and at least one fatty acid", namely saturated fatty acids and unsaturated fatty acids, and in consideration of the potential for degradation by oxidation and the like, the ester is preferably a glycerin and fatty acid ester, which is derived from a saturated fatty acid, i.e., an ester of glycerin and a saturated fatty acid.

Also, in order to lower the IOB and result in greater hydrophobicity, the ester of glycerin and a fatty acid is preferably a diester or triester, and more preferably a triester.

A triester of glycerin and a fatty acid is also known as a triglyceride, and examples include triesters of glycerin and octanoic acid ($C_8$), triesters of glycerin and decanoic acid ($C_{10}$), triesters of glycerin and dodecanoic acid ($C_{12}$), triesters of glycerin and 2 or more different fatty acids, and mixtures of the foregoing.

Examples of triesters of glycerin and 2 or more fatty acids include triesters of glycerin with octanoic acid ($C_8$) and decanoic acid ($C_{10}$), triesters of glycerin with octanoic acid ($C_8$), decanoic acid ($C_{10}$) and dodecanoic acid ($C_{12}$), and triesters of glycerin with octanoic acid ($C_8$), decanoic acid ($C_{10}$), dodecanoic acid (C12), tetradecanoic acid ($C_{14}$), hexadecanoic acid ($C_{16}$) and octadecanoic acid ($C_{18}$).

In order to obtain a melting point of about 45° C. or less, preferred triesters of glycerin and fatty acids are those with no more than about 40 as the total number of carbons of the fatty acid consisting of the triester of glycerin and the fatty acid, i.e., the total number of carbons of the $R^5C$, $R^6C$ and $R^7C$ sections in formula (5).

In a triester of glycerin and a fatty acid, the IOB value is 0.60 when the total number of carbons of the fatty acid consisting of the triester of glycerin and the fatty acid, i.e., the total number of carbons of the $R^5C$, $R^6C$ and $R^7C$ portions in formula (5), is 12. Thus, when the total number of carbons of the fatty acid consisting of the triester of the glycerin and fatty acid is approximately 12 or greater, the IOB satisfies the condition of being within about 0.00 to 0.60.

Triesters of glycerin and fatty acids, being aliphatic and therefore potential constituent components of the human body are preferred from the viewpoint of safety.

Commercial products of triesters of glycerin and fatty acids include tri-coconut fatty acid glycerides, NA36, PANACET 800, PANACET 800B and PANACET 810S, and tri-C2L oil fatty acid glycerides and tri-CL oil fatty acid glycerides (all products of NOF Corp.).

A diester of glycerin and a fatty acid is also known as a diglyceride, and examples include diesters of glycerin and decanoic acid ($C_{10}$), diesters of glycerin and dodecanoic acid ($C_{12}$), diesters of glycerin and hexadecanoic acid ($C_{16}$), diesters of glycerin and 2 or more different fatty acids, and mixtures of the foregoing.

In a diester of glycerin and a fatty acid, the IOB is 0.58 if the total number of carbons of the fatty acid consisting of the diester of the glycerin and fatty acid, i.e., the total number of carbons of the $R^5C$ and $R^6C$ portions in formula (6), is 16. Thus, when the total number of carbons of the fatty acid consisting of the diester of the glycerin and fatty acid is approximately 16 or greater, the IOB satisfies the condition of being about 0.00 to 0.60.

Monoesters of glycerin and fatty acids are also known as monoglycerides, and examples include glycerin and eicosanoic acid ($C_{20}$) monoester, and glycerin and docosanoic acid ($C_{22}$) monoester.

In a monoester of glycerin and a fatty acid, the IOB is 0.59 if the total number of carbons of the fatty acid consisting of the monoester of the glycerin and fatty acid, i.e. the number of carbons of the $R^5C$ portion in formula (7), is 19. Thus, when the number of carbons of the fatty acid consisting of the monoester of the glycerin and fatty acid is approximately 19 or greater, the IOB satisfies the condition of being about 0.00 to 0.60.

[($a_3$) Ester of a Chain Hydrocarbon Diol and at Least One Fatty Acid]

Examples of an ester of a chain hydrocarbon diol and at least one fatty acid include monoesters and diesters of fatty acids with $C_2$-$C_6$ chain hydrocarbon diols, such as $C_2$-$C_6$ glycols, including ethylene glycol, propylene glycol, butylene glycol, pentylene glycol and hexylene glycol.

Specifically, examples of an ester of a chain hydrocarbon diol and at least one fatty acid include diesters of $C_2$-$C_6$ glycols and fatty acids, represented by the following formula (8):

$$R^8COOC_kH_{2k}OCOR^9 \qquad (8)$$

wherein k represents an integer of 2-6, and $R^8$ and $R^9$ each represent a chain hydrocarbon, and monoesters of $C_2$-$C_6$ glycols and fatty acids, represented by the following formula (9):

$$R^8COOC_kH_{2k}OH \qquad (9)$$

wherein k represents an integer of 2-6, and $R^8$ is a chain hydrocarbon.

The fatty acid to be esterified in an ester of a $C_2$-$C_6$ glycol and a fatty acid (corresponding to $R^8COOH$ and $R^9COOH$ in formula (8) and formula (9)) is not particularly restricted so long as the ester of the $C_2$-$C_6$ glycol and fatty acid satisfies the conditions for the IOB, melting point and water solubility, and for example, there may be mentioned the fatty acids mentioned above for the "($a_1$) Ester of a chain hydrocarbon tetraol and at least one fatty acid", namely saturated fatty acids and unsaturated fatty acids, and in consideration of the potential for degradation by oxidation and the like, it is preferably a saturated fatty acid.

In a diester of butylene glycol (k=4) and a fatty acid represented by formula (8), IOB is 0.60 when the total number of carbons of the $R^8C$ and $R^9C$ portions is 6. Thus, when the total number of carbon atoms in a diester of butylene glycol (k=4) and a fatty acid represented by formula (8) is approximately 6 or greater, the IOB satisfies the condition of being about 0.00-0.60. In a monoester of ethylene glycol (k=2) and a fatty acid represented by formula (9), IOB is 0.57 when the total number of carbons of the $R^8C$ portion is 12. Thus, when the total number of carbon atoms in the fatty acid consisting of a monoester of ethylene glycol (k=2) and a fatty acid represented by formula (9) is approximately 12 or greater, the IOB satisfies the condition of being about 0.00-0.60.

Considering the potential for degradation by oxidation and the like, the ester of the $C_2$-$C_6$ glycol and fatty acid is preferably a $C_2$-$C_6$ glycol and fatty acid ester derived from a saturated fatty acid, or in other words, an ester of a $C_2$-$C_6$ glycol and a saturated fatty acid.

Also, in order to lower the IOB and result in greater hydrophobicity, the ester of the $C_2$-$C_6$ glycol and fatty acid is preferably a glycol and fatty acid ester derived from a glycol with a greater number of carbons, such as an ester of a glycol and a fatty acid derived from butylene glycol, pentylene glycol or hexylene glycol.

Also, in order to lower the IOB and result in greater hydrophobicity, the ester of a $C_2$-$C_6$ glycol and fatty acid is preferably a diester.

Examples of commercial products of esters of $C_2$-$C_6$ glycols and fatty acids include COMPOL BL and COMPOL BS (both products of NOF Corp.).

[(B) Ether of (B1) a Compound Having a Chain Hydrocarbon Moiety and 2-4 Hydroxyl Groups Substituted for Hydrogens on the Chain Hydrocarbon Moiety and (B2) a Compound Having a Chain Hydrocarbon Moiety and 1 Hydroxyl Group Substituted for a Hydrogen on the Chain Hydrocarbon Moiety]

In the (B) ether of (B1) a compound having a chain hydrocarbon moiety and 2-4 hydroxyl groups substituted for hydrogens on the chain hydrocarbon moiety and (B2) a compound having a chain hydrocarbon moiety and 1 hydroxyl group substituted for a hydrogen on the chain hydrocarbon moiety (hereunder also referred to as "compound (B)"), it is not necessary for all of the hydroxyl groups to be etherified so long as the IOB, melting point and water solubility are within the aforementioned ranges.

Examples of (B1) a compound having a chain hydrocarbon moiety and 2-4 hydroxyl groups substituted for hydrogens on the chain hydrocarbon moiety (hereunder also referred to as "compound (B1)") include those mentioned for "compound (A)" as compound (A1), such as pentaerythritol, glycerin and glycol.

Examples of (B2) a compound having a chain hydrocarbon moiety and 1 hydroxyl group substituted for a hydrogen on the chain hydrocarbon moiety (hereunder also referred to as "compound (B2)") include compounds wherein 1 hydrogen on the hydrocarbon is substituted with 1 hydroxyl group (—OH), such as aliphatic monohydric alcohols, including saturated aliphatic monohydric alcohols and unsaturated aliphatic monohydric alcohols.

Examples of saturated aliphatic monohydric alcohols include $C_1$-$C_{20}$ saturated aliphatic monohydric alcohols, such as methyl alcohol ($C_1$) ($C_1$ representing the number of carbon atoms, same hereunder), ethyl alcohol ($C_2$), propyl alcohol ($C_3$) and its isomers, including isopropyl alcohol ($C_3$), butyl alcohol ($C_4$) and its isomers, including sec-butyl alcohol ($C_4$) and tert-butyl alcohol ($C_4$), pentyl alcohol ($C_5$), hexyl alcohol ($C_6$), heptyl alcohol ($C_7$), octyl alcohol ($C_8$) and its isomers, including 2-ethylhexyl alcohol ($C_8$), nonyl alcohol ($C_9$), decyl alcohol ($C_{10}$), dodecyl alcohol ($C_{12}$), tetradecyl alcohol ($C_{14}$), hexadecyl alcohol ($C_{16}$), heptadecyl alcohol ($C_{17}$), octadecyl alcohol ($C_{18}$) and eicosyl alcohol ($C_{20}$), as well as their isomers other than those mentioned.

Unsaturated aliphatic monohydric alcohols include those wherein 1 C—C single bond of a saturated aliphatic monohydric alcohol mentioned above is replaced with a C=C double bond, such as oleyl alcohol, and for example, such alcohols are commercially available by New Japan Chemical Co., Ltd. as the RIKACOL Series and UNJECOL Series.

Examples for compound (B) include ($b_1$) an ether of a chain hydrocarbon tetraol and at least one aliphatic monohydric alcohol, such as monoethers, diethers, triethers and tetraethers, preferably diethers, triethers and tetraethers, more preferably triethers and tetraethers and even more preferably tetraethers, ($b_2$) an ether of a chain hydrocarbon triol and at least one aliphatic monohydric alcohol, such as monoethers, diethers and triethers, preferably diethers and triethers and more preferably triethers, and ($b_3$) an ether of a chain hydrocarbon diol and at least one aliphatic monohydric alcohol, such as monoethers and diethers, and preferably diethers.

Examples of an ether of a chain hydrocarbon tetraol and at least one aliphatic monohydric alcohol include tetraethers, triethers, diethers and monoethers of pentaerythritol and aliphatic monohydric alcohols, represented by the following formulas (10)-(13):

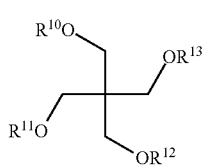

(10)

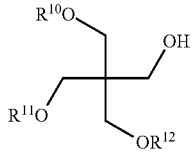

(11)

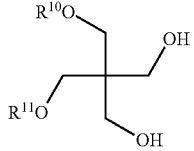

(12)

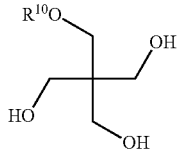

(13)

wherein $R^{10}$-$R^{13}$ each represent a chain hydrocarbon.

Examples of an ether of a chain hydrocarbon triol and at least one aliphatic monohydric alcohol include triethers, diethers and monoethers of glycerin and aliphatic monohydric alcohols, represented by the following formulas (14)-(16):

$$\begin{array}{l} CH_2OR^{14} \\ | \\ CHOR^{15} \\ | \\ CH_2OR^{16} \end{array}$$ (14)

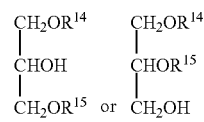

(15)

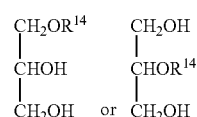

(16)

wherein $R^{14}$-$R^{16}$ each represent a chain hydrocarbon.

Examples of an ether of a chain hydrocarbon diol and at least one aliphatic monohydric alcohol include diethers of $C_2$-$C_6$ glycols and aliphatic monohydric alcohols, represented by the following formula (17):

$$R^{17}OC_nH_{2n}OR^{18}$$ (17)

wherein n is an integer of 2-6, and $R^{17}$ and $R^{18}$ are each a chain hydrocarbon, and monoethers of $C_2$-$C_6$ glycols and aliphatic monohydric alcohols, represented by the following formula (18):

$$R^{17}OC_nH_{2n}OH$$ (18)

wherein n is an integer of 2-6, and $R^{17}$ is a chain hydrocarbon.

In the tetraether of pentaerythritol and an aliphatic monohydric alcohol, the IOB is 0.44 when the total number of carbon atoms of the aliphatic monohydric alcohol consisting of the tetraether of pentaerythritol and the aliphatic monohydric alcohol, i.e., the total number of carbon atoms of the $R^{10}$, $R^{11}$, $R^{12}$ and $R^{13}$ portions in formula (10), is 4. Thus, when the total number of carbon atoms of the aliphatic monohydric alcohol consisting of a tetraether of pentaerythritol and an aliphatic monohydric alcohol is approximately 4 or greater, the IOB value satisfies the condition of being within about 0.00 to 0.60.

In the triether of pentaerythritol and an aliphatic monohydric alcohol, the IOB is 0.57 when the total number of carbon atoms of the aliphatic monohydric alcohol consisting of the triether of pentaerythritol and the aliphatic monohydric alcohol, i.e., the total number of carbon atoms of the $R^{10}$, $R^{11}$ and $R^{12}$ portions in formula (11), is 9. Thus, when the total number of carbon atoms of the aliphatic monohydric alcohol consisting of a triether of pentaerythritol and an aliphatic monohydric alcohol is approximately 9 or greater, the IOB value satisfies the condition of being within about 0.00 to 0.60.

In the diether of pentaerythritol and an aliphatic monohydric alcohol, the IOB is 0.60 when the total number of carbon atoms of the aliphatic monohydric alcohol consisting of the diether of pentaerythritol and the aliphatic monohydric alcohol, i.e., the total number of carbon atoms of the $R^{10}$ and $R^{11}$ portions in formula (12), is 15. Thus, when the total number of carbon atoms of the aliphatic monohydric alcohol consisting of a diether of pentaerythritol and an aliphatic monohydric alcohol is approximately 15 or greater, the IOB value satisfies the condition of being within about 0.00 to 0.60.

In the monoether of pentaerythritol and an aliphatic monohydric alcohol, the IOB is 0.59 when the number of carbon atoms of the aliphatic monohydric alcohol consisting of the monoether of pentaerythritol and the aliphatic monohydric alcohol, i.e. the number of carbon atoms of the $R^{10}$ portion in formula (13), is 22. Thus, when the total number of carbon atoms of the aliphatic monohydric alcohol consisting of a monoether of pentaerythritol and an aliphatic monohydric alcohol is approximately 22 or greater, the IOB value satisfies the condition of being within about 0.00 to 0.60.

In the triether of glycerin and an aliphatic monohydric alcohol, the IOB is 0.50 when the total number of carbon atoms of the aliphatic monohydric alcohol consisting of the triether of glycerin and the aliphatic monohydric alcohol, i.e., the total number of carbon atoms of the $R^{14}$, $R^{15}$ and $R^{16}$ portions in formula (14), is 3. Thus, when the total number of carbon atoms of the aliphatic monohydric alcohol consisting of a triether of glycerin and an aliphatic monohydric alcohol is approximately 3 or greater, the IOB value satisfies the condition of being within about 0.00 to 0.60.

In the diether of glycerin and an aliphatic monohydric alcohol, the IOB is 0.58 when the total number of carbon atoms of the aliphatic monohydric alcohol consisting of the diether of glycerin and the aliphatic monohydric alcohol, i.e., the total number of carbon atoms of the $R^{14}$ and $R^{15}$ portions in formula (15), is 9. Thus, when the total number of carbon atoms of the aliphatic monohydric alcohol consisting of a diether of glycerin and an aliphatic monohydric alcohol is approximately 9 or greater, the IOB value satisfies the condition of being within about 0.00 to 0.60.

In the monoether of glycerin and an aliphatic monohydric alcohol, the IOB is 0.58 when the number of carbon atoms of the aliphatic monohydric alcohol consisting of the monoether of glycerin and the aliphatic monohydric alcohol, i.e., the number of carbon atoms of the $R^{14}$ portion in formula (16), is 16. Thus, when the total number of carbon atoms of the aliphatic monohydric alcohol consisting of a monoether of glycerin and an aliphatic monohydric alcohol is approximately 16 or greater, the IOB value satisfies the condition of being within about 0.00 to 0.60.

In a diether of butylene glycol (n=4) and aliphatic monohydric alcohol represented by formula (17), the IOB is 0.33 when the total number of carbon atoms of the $R^{17}$ and $R^{18}$ portions is 2. Thus, when the number of carbon atoms of the aliphatic monohydric alcohol in a diether of butylene glycol (n=4) and an aliphatic monohydric alcohol represented by formula (17) is approximately 2 or greater, the IOB value satisfies the condition of being within about 0.00-0.60. Also, in a monoether of ethylene glycol (n=2) and aliphatic monohydric alcohol represented by formula (18), the IOB is 0.60 when the number of carbon atoms of the $R^{17}$ portion is 8. Thus, when the number of carbon atoms of the aliphatic monohydric alcohol consisting of a monoether of ethylene glycol (n=2) and an aliphatic monohydric alcohol represented by formula (18) is approximately 8 or greater, the IOB value satisfies the condition of being within about 0.00 to 0.60.

Compound (B) may be produced by dehydrating condensation of compound (B1) and compound (B2) in the presence of an acid catalyst.

[(C) Ester of (C1) a Carboxylic Acid, Hydroxy Acid, Alkoxy Acid or Oxoacid Comprising a Chain Hydrocarbon Moiety and 2-4 Carboxyl Groups Substituted for Hydrogens on the Chain Hydrocarbon Moiety and (C2) a Compound Having a Chain Hydrocarbon Moiety and 1 Hydroxyl Group Substituted for a Hydrogen on the Chain Hydrocarbon Moiety]

In the (C) ester of (C1) a carboxylic acid, hydroxy acid, alkoxy acid or oxoacid comprising a chain hydrocarbon moiety and 2-4 carboxyl groups substituted for hydrogens on the chain hydrocarbon moiety and (C2) a compound having a chain hydrocarbon moiety and 1 hydroxyl group substituted for a hydrogen on the chain hydrocarbon moiety (hereunder also referred to as "compound (C)"), it is not necessary for all of the carboxyl groups to be esterified so long as the IOB, melting point and water solubility are within the aforementioned ranges.

Examples of (C1) a carboxylic acid, hydroxy acid, alkoxy acid or oxoacid comprising a chain hydrocarbon moiety and 2-4 carboxyl groups substituted for hydrogens on the chain hydrocarbon moiety (hereunder also referred to as "compound (C1)") include chain hydrocarbon carboxylic acids with 2-4 carboxyl groups, such as chain hydrocarbon dicarboxylic acids including alkanedicarboxylic acids, such as ethanedioic acid, propanedioic acid, butanedioic acid, pentanedioic acid, hexanedioic acid, heptanedioic acid, octanedioic acid, nonanedioic acid and decanedioic acid, chain hydrocarbon tricarboxylic acids, including alkanetricarboxylic acids, such as propanetrioic acid, butanetrioic acid, pentanetrioic acid, hexanetrioic acid, heptanetrioic acid, octanetrioic acid, nonanetrioic acid and decanetrioic acid, and chain hydrocarbon tetracarboxylic acids, including alkanetetracarboxylic acids, such as butanetetraoic acid, pentanetetraoic acid, hexanetetraoic acid, heptanetetraoic acid, octanetetraoic acid, nonanetetraoic acid and decanetetraoic acid.

Compound (C1) includes chain hydrocarbon hydroxy acids with 2-4 carboxyl groups, such as malic acid, tartaric acid, citric acid and isocitric acid, chain hydrocarbon alkoxy acids with 2-4 carboxyl groups, such as O-acetylcitric acid, and chain hydrocarbon oxoacids with 2-4 carboxyl groups.

(C2) Compound having a chain hydrocarbon moiety and 1 hydroxyl group substituted for a hydrogen on the chain hydrocarbon moiety includes those mentioned for "compound (B)", such as aliphatic monohydric alcohols.

Compound (C) may be ($c_1$) an ester, for example a monoester, diester, triester or tetraester, preferably a diester, triester or tetraester, more preferably a triester or tetraester and even more preferably a tetraester, of a chain hydrocarbon tetracarboxylic acid, hydroxy acid, alkoxy acid or oxoacid with 4 carboxyl groups, and at least one aliphatic monohydric alcohol, ($c_2$) an ester, for example, a monoester, diester or triester, preferably a diester or triester and more preferably a triester, of a chain hydrocarbon tricarboxylic acid, hydroxy acid, alkoxy acid or oxoacid with 3 carboxyl groups, and at least one aliphatic monohydric alcohol, or ($c_3$) an ester, for example, a monoester or diester, and preferably a diester, of a chain hydrocarbon dicarboxylic acid, hydroxy acid, alkoxy acid or oxoacid with 2 carboxyl groups, and at least one aliphatic monohydric alcohol.

Examples for compound (C) include dioctyl adipate, diisostearyl malate, tributyl citrate and tributyl O-acetylcitrate, of which commercially available products exist.

[(D) Compound Having a Chain Hydrocarbon Moiety and One Bond Selected from the Group Consisting of an Ether Bond (—O—), Carbonyl Bond (—CO—), Ester Bond (—COO—) and Carbonate Bond (—OCOO—) Inserted Between a C—C Single Bond of the Chain Hydrocarbon Moiety]

The (D) compound having a chain hydrocarbon moiety and one bond selected from the group consisting of an ether bond (—O—), carbonyl bond (—CO—), ester bond (—COO—) and carbonate bond (—OCOO—) inserted between a C—C single bond of the chain hydrocarbon moiety (hereunder also referred to as "compound (D)") may be ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, or ($d_4$) a dialkyl carbonate.

[($d_1$) Ether of an Aliphatic Monohydric Alcohol and an Aliphatic Monohydric Alcohol]

Ethers of an aliphatic monohydric alcohol and an aliphatic monohydric alcohol include compounds having the following formula (19):

$$R^{19}OR^{20} \qquad (19)$$

wherein $R^{19}$ and $R^{20}$ each represent a chain hydrocarbon.

The aliphatic monohydric alcohol consisting of the ether (corresponding to $R^{19}OH$ and $R^{20}OH$ in formula (19)) is not particularly restricted so long as the ether satisfies the conditions for the IOB, melting point and water solubility, and for example, it may be one of the aliphatic monohydric alcohols mentioned for "compound (B)".

In an ether of an aliphatic monohydric alcohol and an aliphatic monohydric alcohol, the IOB is 0.50 when the total number of carbon atoms of the aliphatic monohydric alcohols consisting of the ether, i.e., the total number of carbons of the $R^{19}$ and $R^{20}$ portions in formula (19), is 2, and therefore when the total number of carbons of the aliphatic monohydric alcohols consisting of the ether is about 2 or greater, this condition for the IOB is satisfied. However, when the total number of carbons of the aliphatic monohydric alcohols consisting of the ether is about 6, the water solubility is as high as about 2 g, which is problematic from the viewpoint of vapor pressure as well. In order to satisfy the condition of a water solubility of about 0.00-0.05 g, the total number of carbons of the aliphatic monohydric alcohols consisting of the ether is preferably about 8 or greater.

[($d_2$) Dialkyl Ketone]

The dialkyl ketone may be a compound of the following formula (20):

$$R^{21}COR^{22} \qquad (20)$$

wherein $R^{21}$ and $R^{22}$ are each an alkyl group.

In a dialkyl ketone, the IOB is 0.54 when the total number of carbon atoms of $R^{21}$ and $R^{22}$ is 5, and therefore this condition for the IOB is satisfied if the total number of carbons is about 5 or greater. However, when the total number of carbons of dialkyl ketone is about 5, the water solubility is as high as about 2 g. Therefore, in order to satisfy the condition of a water solubility of about 0.00-0.05 g, the total number of carbons of dialkyl ketone is preferably about 8 or greater. In consideration of vapor pressure, the number of carbon atoms of dialkyl ketone is preferably about 10 or greater and more preferably about 12 or greater.

If the total number of carbon atoms of dialkyl ketone is about 8, such as in 5-nonanone, for example, the melting point is approximately –50° C. and the vapor pressure is about 230 Pa at 20° C.

The dialkyl ketone may be a commercially available product, or it may be obtained by a known method, such as by oxidation of a secondary alcohol with chromic acid or the like.

[($d_3$) Ester of a Fatty Acid and an Aliphatic Monohydric Alcohol]

Examples of esters of a fatty acid and an aliphatic monohydric alcohol include compounds having the following formula (21):

$$R^{23}COOR^{24} \qquad (21)$$

wherein $R^{23}$ and $R^{24}$ each represent a chain hydrocarbon.

Examples of fatty acids consisting of these esters (corresponding to $R^{23}COOH$ in formula (21)) include the fatty acids mentioned for the "($a_1$) an ester of a chain hydrocarbon tetraol and at least one fatty acids", and specifically these include saturated fatty acids and unsaturated fatty acids, with saturated fatty acids being preferred in consideration of the potential for degradation by oxidation and the like. The aliphatic monohydric alcohol consisting of the ester (corresponding to $R^{24}OH$ in formula (21)) may be one of the aliphatic monohydric alcohols mentioned for "compound (B)".

In an ester of such a fatty acid and aliphatic monohydric alcohol, the IOB is 0.60 when the total number of carbon atoms of the fatty acid and aliphatic monohydric alcohol, i.e. the total number of carbon atoms of the $R^{23}C$ and $R^{24}$ portions in formula (21), is 5, and therefore this condition for the IOB is satisfied when the total number of carbon atoms of the $R^{23}C$ and $R^{24}$ portions is about 5 or greater. However, with butyl acetate in which the total number of carbon atoms is 6, the vapor pressure is high at greater than 2,000 Pa. In consideration of vapor pressure, therefore, the total number of carbon atoms is preferably about 12 or greater. If the total number of carbon atoms is about 11 or greater, it will be possible to satisfy the condition of a water solubility of about 0.00-0.05 g.

Examples of esters of such fatty acids and aliphatic monohydric alcohols include esters of dodecanoic acid ($C_{12}$) and dodecyl alcohol ($C_{12}$) and esters of tetradecanoic acid ($C_{14}$) and dodecyl alcohol ($C_{12}$), and examples of commercial products of esters of such fatty acids and aliphatic monohydric alcohols include ELECTOL WE20 and ELECTOL WE40 (both products of NOF Corp.).

[($d_4$) Dialkyl Carbonate]

The dialkyl carbonate may be a compound of the following formula (22):

$$R^{25}OC(=O)OR^{26} \qquad (22)$$

wherein $R^{25}$ and $R^{26}$ are each an alkyl group.

In a dialkyl carbonate, the IOB is 0.57 when the total number of carbon atoms of $R^{25}$ and $R^{26}$ is 6, and therefore this condition for the IOB is satisfied if the total number of carbons of $R^{25}$ and $R^{26}$ is about 6 or greater.

In consideration of water solubility, the total number of carbon atoms of $R^{25}$ and $R^{26}$ is preferably about 7 or greater and more preferably about 9 or greater.

The dialkyl carbonate may be a commercially available product, or it may be synthesized by reaction between phosgene and an alcohol, reaction between formic chloride and an alcohol or alcoholate, or reaction between silver carbonate and an alkyl iodide.

[(E) Polyoxy $C_2$-$C_6$ Alkylene Glycol, or Alkyl Ester or Alkyl Ether Thereof]

The (E) polyoxy $C_2$-$C_6$ alkylene glycol, or alkyl ester or alkyl ether thereof (hereunder also referred to as "compound (E)") may be ($e_1$) a polyoxy $C_2$-$C_6$ alkylene glycol, ($e_2$) an ester of a polyoxy $C_2$-$C_6$ alkylene glycol and at least one fatty acid, ($e_3$) an ether of a polyoxy $C_2$-$C_6$ alkylene glycol and at least one aliphatic monohydric alcohol, ($e_4$) an ester of a polyoxy $C_2$-$C_6$ alkylene glycol and a chain hydrocarbon tetracarboxylic acid, chain hydrocarbon tricarboxylic acid or chain hydrocarbon dicarboxylic acid, or ($e_5$) an ether of a polyoxy $C_2$-$C_6$ alkylene glycol and a chain hydrocarbon tetraol, chain hydrocarbon triol or chain hydrocarbon diol. These will now be explained.

[($e_1$) Polyoxy $C_2$-$C_6$ Alkylene Glycol]

Polyoxy $C_2$-$C_6$ alkylene glycols refer to i) one or more homopolymers having a unit selected from the group consisting of oxy $C_2$-$C_6$ alkylene units, such as oxyethylene unit, oxypropylene unit, oxybutylene unit, oxypentylene unit and oxyhexylene unit and having hydroxyl groups at both ends, ii) one or more block copolymers having 2 or more units selected from oxy $C_2$-$C_6$ alkylene units described above and oxyhexylene unit and having hydroxyl groups at both ends, or iii) random copolymers having 2 or more units selected from oxy $C_2$-$C_6$ alkylene units described above and having hydroxyl groups at both ends.

The oxy $C_2$-$C_6$ alkylene units are preferably oxypropylene unit, oxybutylene unit, oxypentylene unit or oxyhexylene unit, and more preferably oxybutylene unit, oxypentylene unit and oxyhexylene unit, from the viewpoint of reducing the value of IOB.

The polyoxy $C_2$-$C_6$ alkylene glycol can be represented by the following formula (23):

$$HO-(C_mH_{2m}O)_n-H \quad (23)$$

wherein m represents an integer of 2-6.

The present inventors have confirmed that in polyethylene glycol (corresponding to the homopolymer of formula (23) where m=2), when n≥45 (the weight-average molecular weight exceeds about 2,000), the condition for IOB of about 0.00 to about 0.60 is satisfied, but the condition for the water solubility is not satisfied even when the weight-average molecular weight exceeds about 4,000. Therefore, ethylene glycol homopolymer is not included in the ($e_1$) polyoxy $C_2$-$C_6$ alkylene glycol, and ethylene glycol should be included in the ($e_1$) polyoxy $C_2$-$C_6$ alkylene glycol only as a copolymer or random polymer with another glycol.

Thus, homopolymers of formula (23) may include propylene glycol, butylene glycol, pentylene glycol or hexylene glycol homopolymer.

For this reason, m in formula (23) is about 3 to 6 and preferably about 4 to 6, and n is 2 or greater.

The value of n in formula (23) is a value such that the polyoxy $C_2$-$C_6$ alkylene glycol has an IOB of about 0.00-0.60, a melting point of about 45° C. or less and a water solubility of about 0.00-0.05 g in 100 g of water at 25° C.

For example, when formula (23) is polypropylene glycol (m=3, homopolymer), the IOB is 0.58 when n=12. Thus, when formula (23) is polypropylene glycol (m=3, homopolymer), the condition for the IOB is satisfied when m is equal to or greater than about 12.

Also, when formula (23) is polybutylene glycol (m=4, homopolymer), the IOB is 0.57 when n=7. Thus, when formula (23) is polybutylene glycol (m=4, homopolymer), the condition for the IOB is satisfied when n is equal to or greater than about 7.

From the viewpoint of IOB, melting point and water solubility, the weight-average molecular weight of the polyoxy $C_4$-$C_6$ alkylene glycol is preferably between about 200 and about 10,000, more preferably between about 250 and about 8,000, and even more preferably in the range of about 250 to about 5,000.

Also from the viewpoint of IOB, melting point and water solubility, the weight-average molecular weight of a polyoxy $C_3$ alkylene glycol, i.e. polypropylene glycol, is preferably between about 1,000 and about 10,000, more preferably between about 3,000 and about 8,000, and even more preferably between about 4,000 and about 5,000. This is because if the weight-average molecular weight is less than about 1,000, the condition for the water solubility will not be satisfied, and a larger weight-average molecular weight will particularly tend to increase the migration rate into the absorbent body and the whiteness of the top sheet.

Examples of commercial products of polyoxy $C_2$-$C_6$ alkylene glycols include UNIOL™ D-1000, D-1200, D-2000, D-3000, D-4000, PB-500, PB-700, PB-1000 and PB-2000 (all products of NOF Corp.).

[($e_2$) Ester of a Polyoxy $C_2$-$C_6$ Alkylene Glycol and at Least One Fatty Acid]

Examples of an ester of a polyoxy $C_2$-$C_6$ alkylene glycol and at least one fatty acids include the polyoxy $C_2$-$C_6$ alkylene glycols mentioned for "($e_1$) Polyoxy $C_2$-$C_6$ alkylene glycol" in which one or both OH ends have been esterified with fatty acids, i.e. monoesters and diesters.

Examples of fatty acids to be esterified in the ester of a polyoxy $C_2$-$C_6$ alkylene glycol and at least one fatty acid include the fatty acids mentioned for the "($a_1$) Ester of a chain hydrocarbon tetraol and at least one fatty acid", and specifically these include saturated fatty acids and unsaturated fatty acids, with saturated fatty acids being preferred in consideration of the potential for degradation by oxidation and the like.

An example of a commercially available ester of a polyoxy $C_2$-$C_6$ alkylene glycol and a fatty acid is WILBRITE cp9 (product of NOF Corp.).

[($e_3$) Ether of a Polyoxy $C_2$-$C_6$ Alkylene Glycol and at Least One Aliphatic Monohydric Alcohol]

Examples of an ether of a polyoxy $C_2$-$C_6$ alkylene glycols and at least one aliphatic monohydric alcohol include the polyoxy $C_2$-$C_6$ alkylene glycols mentioned for "($e_1$) Polyoxy $C_2$-$C_6$ alkylene glycol" wherein one or both OH ends have been etherified by an aliphatic monohydric alcohol, i.e. monoethers and diethers.

In an ether of a polyoxy $C_2$-$C_6$ alkylene glycol and at least one aliphatic monohydric alcohol, the aliphatic monohydric alcohol to be etherified may be an aliphatic monohydric alcohol among those mentioned for "compound (B)".

[($e_4$) Ester of a Polyoxy $C_2$-$C_6$ Alkylene Glycol and a Chain Hydrocarbon Tetracarboxylic Acid, Chain Hydrocarbon Tricarboxylic Acid or Chain Hydrocarbon Dicarboxylic Acid]

The polyoxy $C_2$-$C_6$ alkylene glycol to be esterified for the aforementioned ester of a polyoxy $C_2$-$C_6$ alkylene glycol and a chain hydrocarbon tetracarboxylic acid, chain hydrocarbon tricarboxylic acid or chain hydrocarbon dicarboxylic acid may be any of the polyoxy $C_2$-$C_6$ alkylene glycols mentioned above under "($e_1$) Polyoxy $C_2$-$C_6$ alkylene glycol". Also, the chain hydrocarbon tetracarboxylic acid, chain hydrocarbon tricarboxylic acid or chain hydrocarbon dicarboxylic acid to be esterified may be any of those mentioned above for "compound (C)".

The ester of a polyoxy $C_2$-$C_6$ alkylene glycol and a chain hydrocarbon tetracarboxylic acid, chain hydrocarbon tricarboxylic acid or chain hydrocarbon dicarboxylic acid may be a commercially available product, or it may be produced by polycondensation of a $C_2$-$C_6$ alkylene glycol with a chain hydrocarbon tetracarboxylic acid, chain hydrocarbon tricarboxylic acid or chain hydrocarbon dicarboxylic acid under known conditions.

[($e_5$) Ether of a Polyoxy $C_2$-$C_6$ Alkylene Glycol and a Chain Hydrocarbon Tetraol, Chain Hydrocarbon Triol or Chain Hydrocarbon Diol]

The polyoxy $C_2$-$C_6$ alkylene glycol to be etherified for the aforementioned ether of a polyoxy $C_2$-$C_6$ alkylene glycol and a chain hydrocarbon tetraol, chain hydrocarbon triol or chain hydrocarbon diol may be any of the polyoxy $C_2$-$C_6$ alkylene glycols mentioned above under "($e_1$) polyoxy $C_2$-$C_6$ alkylene glycol". Also, the chain hydrocarbon tetraol, chain hydrocarbon triol or chain hydrocarbon diol to be etherified may be, for example, pentaerythritol, glycerin or glycol, mentioned above for "compound (A)".

Examples of commercially available ethers of polyoxy $C_2$-$C_6$ alkylene glycols and chain hydrocarbon tetraols, chain hydrocarbon triols and chain hydrocarbon diols include UNILUBE™ 5 TP-300 KB and UNIOL™ TG-3000 and TG-4000 (products of NOF Corp.).

UNILUBE™ 5 TP-300 KB is a compound obtained by polycondensation of 65 mol of propylene glycol and 5 mol of ethylene glycol with 1 mol of pentaerythritol, and it has an IOB of 0.39, a melting point of below 45° C., and a water solubility of less than 0.05 g.

UNIOL™ TG-3000 is a compound obtained by polycondensation of 50 mol of propylene glycol with 1 mol of glycerin, and it has an IOB of 0.42, a melting point of below 45° C., a water solubility of less than 0.05 g, and a weight-average molecular weight of about 3,000.

UNIOL™ TG-4000 is a compound obtained by polycondensation of 70 mol of propylene glycol with 1 mol of glycerin, and it has an IOB of 0.40, a melting point of below 45° C., a water solubility of less than 0.05 g, and a weight-average molecular weight of about 4,000.

The ether of a polyoxy $C_2$-$C_6$ alkylene glycol and a chain hydrocarbon tetraol, chain hydrocarbon triol or chain hydrocarbon diol may also be produced by adding a $C_2$-$C_6$ alkylene oxide to a chain hydrocarbon tetraol, chain hydrocarbon triol or chain hydrocarbon diol under known conditions.

[(F) Chain Hydrocarbon]

The chain hydrocarbon has an inorganic value of 0 and thus an IOB of 0.00, while the water solubility is also approximately 0 g, and therefore if the melting point is about 45° C. or less it may be included among the aforementioned blood modifying agents. Examples of such chain hydrocarbons include ($f_1$) a chain alkane, such as linear alkanes and branched alkanes, and linear alkanes generally include those with no more than 22 carbons, in consideration of a melting point of about 45° C. or less. In consideration of vapor pressure, they generally include those with 13 or more carbons. Branched alkanes generally include those with 22 or more carbons, since their melting points are often lower than linear alkanes, given the same number of carbon atoms.

Examples of commercially available hydrocarbon products include PARLEAM 6 (NOF Corp.).

The blood modifying agent has been found to have at least a function of lowering blood viscosity and surface tension, which will be considered in detail in the examples. Menstrual blood to be absorbed by the absorbent article, unlike ordinary blood, contains proteins of the endometrial wall, for example, which act to bind together blood cells so that the blood cells form a rouleau state. Menstrual blood which is to be absorbed by the absorbent article therefore tends to have high viscosity, and when the top sheet and second sheet are nonwoven fabrics or woven fabric, the menstrual blood becomes clogged between the fibers creating a residual sticky feel for the wearer, while the menstrual blood also diffuses on the surface of the top sheet and tends to leak.

The blood modifying agent which has an IOB of about 0.00 to 0.60 has high organicity and readily infiltrates between blood cells, and it therefore stabilizes the blood cells and can prevent formation of a rouleau structure by the blood cells. For example, with an absorbent article comprising an acrylic super-absorbent polymer, or SAP, absorption of menstrual blood is known to lead to covering of the SAP surface by rouleau-formed blood cells and inhibition of the absorption performance of the SAP, but presumably stabilization of the blood cells allows the absorption performance of the SAP to be exhibited more easily. In addition, the blood modifying agent which has high affinity with erythrocytes protects the erythrocyte membranes, and therefore may minimize destruction of the erythrocytes.

The weight-average molecular weight of the blood modifying agent is preferably about 2,000 or less, and more preferably about 1,000 or less. A high weight-average molecular weight will tend to result in high viscosity of the blood modifying agent, and it will be difficult to lower the viscosity of the blood modifying agent by heating, to a viscosity suitable for coating. As a result, it will sometimes be necessary to dilute the blood modifying agent with a solvent. In addition, if the weight-average molecular weight is higher, tack may result in the blood modifying agent itself, tending to create a feeling of unpleasantness for the wearer.

EXAMPLES

The present invention will now be explained by examples, with the understanding that the present invention is not meant to be limited to the examples.

Example 1

[Data of Blood Modifying Agents]

A commercially available sanitary napkin was prepared. The sanitary napkin was formed from a top sheet, formed of a hydrophilic agent-treated air-through nonwoven fabric (composite fiber composed of polyester and polyethylene terephthalate, basis weight: 35 g/m$^2$), a second sheet, formed of an air-through nonwoven fabric (composite fiber composed of polyester and polyethylene terephthalate, basis weight: 30 g/m$^2$), an absorbent body comprising pulp (basis weight: 150-450 g/m$^2$, increased at the center section), an acrylic super-absorbent polymer (basis weight: 15 g/m$^2$) and tissue as a core wrap, a water-repellent agent-treated side sheet, and a back sheet composed of a polyethylene film.

The blood modifying agents used for testing are listed below.

[($a_1$) Ester of a Chain Hydrocarbon Tetraols and at Least One Fatty Acid]

UNISTAR H-408BRS, product of NOF Corp.
    Pentaerythritol tetra(2-ethylhexanoate), weight-average molecular weight: approximately 640

UNISTAR H-2408BRS-22, product of NOF Corp.
Mixture of pentaerythritol tetra(2-ethylhexanoate) and neopentylglycol di(2-ethylhexanoate) (58:42 as weight ratio), weight-average molecular weight: approximately 520

[($a_2$) Ester of a Chain Hydrocarbon Triols and at Least One Fatty Acid]
Cetiol SB45DEO, Cognis Japan
Glycerin and fatty acid triester, with oleic acid or stearylic acid as the fatty acid.
SOY42, product of NOF Corp.
Glycerin and fatty acid triester with $C_{14}$ fatty acid:$C_{16}$ fatty acid:$C_{18}$ fatty acid:$C_{20}$ fatty acid (including both saturated fatty acids and unsaturated fatty acids) at a mass ratio of about 0.2:11:88:0.8, weight-average molecular weight: 880
Tri-C2L oil fatty acid glyceride, product of NOF Corp.
Glycerin and fatty acid triester with $C_8$ fatty acid:$C_{10}$ fatty acid:$C_{12}$ fatty acid at a mass ratio of about 37:7:56, weight-average molecular weight: approximately 570
Tri-CL oil fatty acid glyceride, product of NOF Corp.
Glycerin and fatty acid triester with $C_8$ fatty acid:$C_{12}$ fatty acid at a mass ratio of about 44:56, weight-average molecular weight: approximately 570
PANACET 810s, product of NOF Corp.
Glycerin and fatty acid triester with $C_8$ fatty acid:$C_{10}$ fatty acid at a mass ratio of about 85:15, weight-average molecular weight: approximately 480
PANACET 800, product of NOF Corp.
Glycerin and fatty acid triester with octanoic acid (C8) as the entire fatty acid portion, weight-average molecular weight: approximately 470
PANACET 800B, product of NOF Corp.
Glycerin and fatty acid triester with 2-ethylhexanoic acid ($C_8$) as the entire fatty acid portion, weight-average molecular weight: approximately 470
NA36, product of NOF Corp.
Glycerin and fatty acid triester with $C_{16}$ fatty acid:$C_{18}$ fatty acid:$C_{20}$ fatty acid (including both saturated fatty acids and unsaturated fatty acids) at a mass ratio of about 5:92:3, weight-average molecular weight: approximately 880
Tri-coconut fatty acid glyceride, product of NOF Corp.
Glycerin and fatty acid triester with $C_8$ fatty acid:$C_{10}$ fatty acid:$C_{12}$ fatty acid:$C_{14}$ fatty acid:$C_{16}$ fatty acid (including both saturated fatty acids and unsaturated fatty acids) at a mass ratio of about 4:8:60:25:3, weight-average molecular weight: 670
Caprylic acid diglyceride, product of NOF Corp.
Glycerin and fatty acid diester with octanoic acid as the fatty acid, weight-average molecular weight: approximately 340

[($a_3$) Ester of a Chain Hydrocarbon Diol and at Least One Fatty Acid]
COMPOL BL, product of NOF Corp.
Dodecanoic acid ($C_{12}$) monoester of butylene glycol, weight-average molecular weight: approximately 270
COMPOL BS, product of NOF Corp.
Octadecanoic acid ($C_{18}$) monoester of butylene glycol, weight-average molecular weight: approximately 350
UNISTAR H-208BRS, product of NOF Corp.
Neopentyl glycol di(2-ethylhexanoate), weight-average molecular weight: approximately 360

[($c_2$) Ester of a Chain Hydrocarbon Tricarboxylic Acid, Hydroxy Acid, Alkoxy Acid or Oxoacid with 3 Carboxyl Groups, and at Least One Aliphatic Monohydric Alcohol]
Tributyl O-acetylcitrate, product of Tokyo Kasei Kogyo Co., Ltd.
Weight-average molecular weight: approximately 400

[($c_3$) Ester of a Chain Hydrocarbon Dicarboxylic Acid, Hydroxy Acid, Alkoxy Acid or Oxoacid with 2 Carboxyl Groups, and at Least One Aliphatic Monohydric Alcohol]
Dioctyl adipate, product of Wako Pure Chemical Industries, Ltd.
Weight-average molecular weight: approximately 380

[($d_3$) Ester of a Fatty Acid and an Aliphatic Monohydric Alcohol]
ELECTOL WE20, product of NOF Corp.
Ester of dodecanoic acid ($C_{12}$) and dodecyl alcohol ($C_{12}$), weight-average molecular weight: approximately 360
ELECTOL WE40, product of NOF Corp.
Ester of tetradecanoic acid ($C_{14}$) and dodecyl alcohol (C12), weight-average molecular weight: approximately 390

[($e_1$) Polyoxy $C_2$-$C_6$ Alkylene Glycol]
UNIOL D-1000, product of NOF Corp.
Polypropylene glycol, weight-average molecular weight: approximately 1,000
UNIOL D-1200, product of NOF Corp.
Polypropylene glycol, weight-average molecular weight: approximately 1,200
UNIOL D-3000, product of NOF Corp.
Polypropylene glycol, weight-average molecular weight: approximately 3,000
UNIOL D-4000, product of NOF Corp.
Polypropylene glycol, weight-average molecular weight: approximately 4,000
UNIOL PB500, product of NOF Corp.
Polybutylene glycol, weight-average molecular weight: approximately 500
UNIOL PB700, product of NOF Corp.
Polyoxybutylene polyoxypropylene glycol, weight-average molecular weight: approximately 700
UNIOL PB1000R, product of NOF Corp.
Polybutylene glycol, weight-average molecular weight: approximately 1000

[($e_2$) Ester of a Polyoxy $C_2$-$C_6$ Alkylene Glycol and at Least One Fatty Acid]
WILBRITE cp9, product of NOF Corp.
Polybutylene glycol compound with OH groups at both ends esterified by hexadecanoic acid ($C_{16}$), weight-average molecular weight: approximately 1,150

[($e_3$) Ether of a Polyoxy $C_2$-$C_6$ Alkylene Glycol and at Least One Aliphatic Monohydric Alcohol]
UNILUBE MS-70K, product of NOF Corp.
Stearyl ether of polypropylene glycol, approximately 15 repeating units, weight-average molecular weight: approximately 1,140

[($e_5$) Ethers of a Polyoxy $C_2$-$C_6$ Alkylene Glycol and a Chain Hydrocarbon Tetraol, Chain Hydrocarbon Triol or Chain Hydrocarbon Diol]
UNILUBE 5TP-300 KB
Polyoxyethylenepolyoxypropylene pentaerythritol ether, produced by addition of 5 mol of ethylene oxide and 65 mol of propylene oxide to 1 mol of pentaerythritol, weight-average molecular weight: 4,130
UNIOL TG-3000, product of NOF Corp.
Glyceryl ether of polypropylene glycol, approximately 16 repeating units, weight-average molecular weight: approximately 3,000
UNIOL TG-4000, product of NOF Corp.

Glyceryl ether of polypropylene glycol, approximately 16 repeating units, weight-average molecular weight: approximately 4,000

[(f₁) Chain Alkane]

PARLEAM 6, product of NOF Corp.
 Branched chain hydrocarbon, produced by copolymerization of liquid isoparaffin, isobutene and n-butene followed by hydrogen addition, polymerization degree: approximately 5-10, weight-average molecular weight: approximately 330

[Other Materials]

NA50, product of NOF Corp.
 Glycerin and fatty acid triester obtained by addition of hydrogen to NA36 for reduced proportion of double bonds from unsaturated fatty acid starting material, weight-average molecular weight: approximately 880

(Caprylic acid/capric acid) monoglyceride, product of NOF Corp.
 Glycerin and fatty acid monoester, with octanoic acid ($C_8$) and decanoic acid ($C_{10}$) at a mass ratio of about 85:15, weight-average molecular weight: approximately 220

Monomuls 90-L2 lauric acid monoglyceride, product of Cognis Japan

Isopropyl citrate, product of Tokyo Kasei Kogyo Co., Ltd.
 Weight-average molecular weight: approximately 230

Diisostearyl malate
 Weight-average molecular weight: approximately 640

UNIOL D-400, product of NOF Corp.
 Polypropylene glycol, weight-average molecular weight: approximately 400

PEG1500, product of NOF Corp.
 Polyethylene glycol, weight-average molecular weight: approximately 1,500-1,600

NONION S-6, product of NOF Corp.
 Polyoxyethylene monostearate, approximately 7 repeating units, weight-average molecular weight: approximately 880

WILBRITE s753, product of NOF Corp.
 Polyoxyethylene polyoxypropylene polyoxybutylene glycerin, weight-average molecular weight: approximately 960

UNIOL TG-330, product of NOF Corp.
 Glyceryl ether of polypropylene glycol, approximately 6 repeating units, weight-average molecular weight: approximately 330

UNIOL TG-1000, product of NOF Corp.
 Glyceryl ether of polypropylene glycol, approximately 16 repeating units, weight-average molecular weight: approximately 1,000

UNILUBE DGP-700, product of NOF Corp.
 Diglyceryl ether of polypropylene glycol, approximately 9 repeating units, weight-average molecular weight: approximately 700

UNIOX HC60, product of NOF Corp.
 Polyoxyethylene hydrogenated castor oil, weight-average molecular weight: approximately 3,570

Vaseline, product of Cognis Japan
 Petroleum-derived hydrocarbon, semi-solid

The IOBs, melting points and water solubilities of the samples are shown in Table 2.

The water solubility was measured by the method described above, and samples that dissolved 24 hours after addition of 20.0 g to 100 g of desalted water were evaluated as "20 g<", and samples of which 0.05 g dissolved in 100 g of desalted water but 1.00 g did not dissolve were evaluated as 0.05-1.00 g.

For the melting point, "<45" indicates a melting point of below 45° C.

The skin contact surface of the top sheet of the sanitary napkin was coated with the aforementioned blood modifying agent. Each blood modifying agent was used directly, when the blood modifying agent was liquid at room temperature, or when the blood modifying agent was solid at room temperature it was heated to its melting point +20° C., and a control seam HMA gun was used for atomization of the blood modifying agent and coating onto the entire skin contact surface of the top sheet to a basis weight of about 5 g/m².

Figure 11:
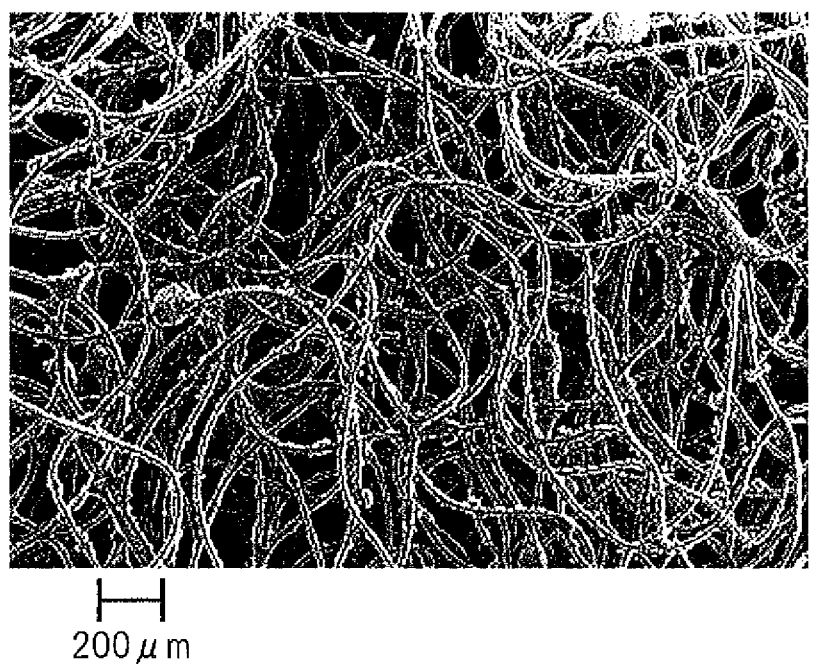
FIG. 11 is an electron micrograph of the skin contact surface of a top sheet in a sanitary napkin wherein the top sheet comprises tri-C2L oil fatty acid glycerides.

FIG. 11 is an electron micrograph of the skin contact surface of a top sheet in a sanitary napkin (No. 2-5) wherein the top sheet comprises tri-C2L oil fatty acid glycerides. As clearly seen in FIG. 11, the tri-C2L oil fatty acid glycerides are adhering onto the fiber surfaces as fine particulates.

The rewetting rate and absorbent body migration rate were measured by the procedure described above. The results are shown in Table 2 below.

[Test Methods]

An acrylic board with an opened hole (200 mm×100 mm, 125 g, with a 40 mm×10 mm hole opened at the center) was placed on a top sheet comprising each blood modifying agent, and 3.0 g of horse EDTA blood at 37±1° C. (obtained by adding ethylenediaminetetraacetic acid (hereunder, "EDTA") to horse blood to prevent coagulation) was dropped through the hole using a pipette (once), and after 1 minute, 3.0 g of horse EDTA blood at 37±1° C. was again added dropwise through the acrylic board hole with a pipette (twice).

After the second dropping of blood, the acrylic board was immediately removed and 10 sheets of filter paper (Advantec Toyo Kaisha, Ltd, Qualitative Filter Paper No. 2, 50 mm×35 mm, total mass of the 10 sheets of filter paper: $FW_0$ (g)) were placed on the location where the blood had been dropped, and then a weight was placed thereover to a pressure of 30 g/cm². After 1 minute, the filter paper was removed, total mass of 10 sheets of filter paper ($FW_1$ (g)) was measured, and the "rewetting rate" was calculated by the following formula.

$$\text{Rewetting rate (mass \%)} = 100 \times [FW_1(g) - FW_0(g)]/6.0 \text{ (g)}$$

In addition to the rewetting rate evaluation, the "absorbent body migration rate" was also measured as the time until migration of blood from the top sheet to the absorbent body after the second dropping of blood. The absorbent body migration rate is the time from introducing the blood onto the top sheet, until the redness of the blood could be seen on the surface and in the interior of the top sheet.

The results for the rewetting rate and absorbent body migration rate are shown below in Table 2.

Next, the whiteness of the skin contact surface of the top sheet after the absorbent body migration rate test was visually evaluated on the following scale.

VG (Very Good): Virtually no redness of blood remaining, and no clear delineation between areas with and without blood.

G (Good): Slight redness of blood remaining, but difficult to delineate between areas with and without blood.

F (Fair): Slight redness of blood remaining, areas with blood discernible.

P (Poor): Redness of blood completely remaining.

The results are summarized in Table 2.

TABLE 2

| No. | Type | Blood modifying agent Product name | IOB | Melting pt. (°C.) | Water solubility (g) | Weight-average mol. wt. | Rewetting rate (%) | Absorbent body migration rate (sec) | Top sheet whiteness |
|---|---|---|---|---|---|---|---|---|---|
| 2-1 | (a₁) | H-408BRS | 0.13 | <−5 | <0.05 | 640 | 1.2 | 3 | VG |
| 2-2 | | H-2408BRS-22 | 0.18 | <−5 | <0.05 | 520 | 2.0 | 3 | VG |
| 2-3 | (a₂) | Cetiol SB45DEO | 0.16 | 44 | <0.05 | | 7.0 | 6 | VG |
| 2-4 | | SOY42 | 0.16 | 43 | <0.05 | 880 | 5.8 | 8 | VG |
| 2-5 | | Tri C2L oil fatty acid glyceride | 0.27 | 37 | <0.05 | 570 | 0.3 | 3 | VG |
| 2-6 | | Tri CL oil fatty acid glyceride | 0.28 | 38 | <0.05 | 570 | 1.7 | 3 | VG |
| 2-7 | | PANACET 810s | 0.32 | −5 | <0.05 | 480 | 2.8 | 3 | VG |
| 2-8 | | PANACET 800 | 0.33 | −5 | <0.05 | 470 | 0.3 | 3 | VG |
| 2-9 | | PANACET 800B | 0.33 | −5 | <0.05 | 470 | 2.0 | 3 | VG |
| 2-10 | | NA36 | 0.16 | 37 | <0.05 | 880 | 3.9 | 5 | VG |
| 2-11 | | Tri-coconut fatty acid glyceride | 0.28 | 30 | <0.05 | 670 | 4.3 | 5 | VG |
| 2-12 | | Caprylic diglyceride | 0.58 | <45 | <0.05 | 340 | 4.2 | 9 | G |
| 2-13 | (a₃) | COMPOL BL | 0.50 | 2 | <0.05 | 270 | 2.0 | 5 | G |
| 2-14 | | COMPOL BS | 0.36 | 37 | <0.05 | 350 | 7.9 | 9 | G |
| 2-15 | | H-208BRS | 0.24 | <−5 | <0.05 | 360 | 2.0 | 5 | VG |
| 2-16 | (c₂) | Tributyl O-acetylcitrate | 0.60 | <45 | <0.05 | 400 | 6.2 | 8 | VG |
| 2-17 | (c₃) | Dioctyl adipate | 0.27 | <45 | <0.05 | 380 | 1.7 | 6 | VG |
| 2-18 | (d₃) | ELECTOL WE20 | 0.13 | 29 | <0.05 | 360 | 1.8 | 5 | VG |
| 2-19 | | ELECTOL WE40 | 0.12 | 37 | <0.05 | 390 | 1.8 | 4 | VG |
| 2-20 | (e₁) | UNIOL D-1000 | 0.51 | <45 | <0.05 | 1,000 | 6.8 | 15 | F |
| 2-21 | | UNIOL D-1200 | 0.48 | <45 | <0.05 | 1,160 | 0.5 | 11 | F |
| 2-22 | | UNIOL D-3000 | 0.39 | <45 | <0.05 | 3,000 | 1.7 | 10 | F |
| 2-23 | | UNIOL D-4000 | 0.38 | <45 | <0.05 | 4,000 | 1.0 | 7 | G |
| 2-24 | (e₁) | UNIOL PB500 | 0.44 | <45 | <0.05 | 500 | 4.5 | 4 | G |
| 2-25 | | UNIOL PB700 | 0.49 | −5 | <0.05 | 700 | 2.8 | 5 | G |
| 2-26 | | UNIOL PB1000R | 0.40 | <45 | <0.05 | 1,000 | 4.0 | 4 | G |
| 2-27 | (e₂) | WILBRITE cp9 | 0.21 | 35 | <0.05 | 1,150 | 1.4 | 3 | G |
| 2-28 | (e₃) | UNILUBE MS-70K | 0.30 | <−10 | <0.05 | 1,140 | 6.7 | 3 | G |
| 2-29 | (e₅) | UNILUBE 5TP-300KB | 0.39 | <45 | <0.05 | 4,130 | 2.0 | 6 | G |
| 2-30 | | UNIOL TG-3000 | 0.42 | <45 | <0.05 | 3,000 | 0.8 | 6 | G |
| 2-31 | | UNIOL TG-4000 | 0.40 | <45 | <0.05 | 4,000 | 2.0 | 6 | G |
| 2-32 | (f₁) | PARLEAM 6 | 0.00 | −5 | <0.05 | 330 | 6.0 | 8 | VG |
| 2-33 | | NA50 | 0.18 | 52 | <0.05 | 880 | 15.5 | 60 | P |
| 2-34 | | (Caprylic/capric) monoglyceride | 1.15 | <45 | 20< | 220 | 4.0 | 4 | P |
| 2-35 | | 90-L2 Lauric acid monoglyceride | 0.87 | 58 | 20< | | 6.2 | 7 | P |
| 2-36 | | Isopropyl citrate | 1.56 | <45 | 20< | 230 | 12.2 | 5 | G |
| 2-37 | | Diisostearyl malate | 0.28 | <45 | 20< | 640 | 5.5 | 8 | F |
| 2-38 | | UNIOL D-400 | 0.76 | <45 | 0.05< | 400 | 8.7 | 40 | P |
| 2-39 | | PEG1500 | 0.78 | 40 | 20< | 1,500–1,600 | 11.0 | 38 | P |
| 2-40 | | NONION S-6 | 0.44 | 37 | 0.05< | 880 | 8.4 | 7 | P |
| 2-41 | | WILBRITE s753 | 0.67 | −5 | 20< | 960 | 9.3 | 9 | F |
| 2-42 | | UNIOL TG-330 | 1.27 | <45 | 0.05< | 330 | — | — | — |
| 2-43 | | UNIOL TG-1000 | 0.61 | <45 | <0.05 | 1,000 | 14.2 | 7 | G |
| 2-44 | | UNILUBE DGP-700 | 0.91 | <0 | 0.05< | 700 | 8.0 | 10 | F |
| 2-45 | | UNIOX HC60 | 0.46 | 33 | 0.05–1.00 | 3,570 | 14.6 | 46 | P |
| 2-46 | | Vaseline | 0.00 | 55 | <0.05 | | 9.7 | 10 | F |
| 2-47 | | None | — | — | — | — | 22.7 | 60< | P |

In the absence of a blood modifying agent, the rewetting rate was 22.7% and the absorbent body migration rate was greater than 60 seconds, but the glycerin and fatty acid triesters all produced rewetting rates of no greater than 7.0% and absorbent body migration rates of no longer than 8 seconds, and therefore significantly improved the absorption performance. Of the glycerin and fatty acid triesters, however, no great improvement in absorption performance was seen with NA50 which had a melting point of above 45° C.

Similarly, the absorption performance was also significantly improved with blood modifying agents having an IOB of about 0.00-0.60, a melting point of about 45° C. or less, and a water solubility of about 0.00-0.05 g in 100 g of water at 25° C.

Example 2

The rewetting rate was evaluated for blood from different animals, by the procedure described above. The following blood was used for the test.
[Animal Species]
(1) Human
(2) Horse
(3) Sheep
[Types of Blood]
  Defibrinated blood: blood sampled and agitated together with glass beads in an Erlenmeyer flask for approximately 5 minutes.
  EDTA blood: 65 mL of venous blood with addition of 0.5 mL of a 12% EDTA•2K isotonic sodium chloride solution.
[Fractionation]
  Serum or blood plasma: Supernatant obtained after centrifugation of defibrinated blood or EDTA blood for 10 minutes at room temperature at about 1900 G.
  Blood cells: Obtained by removing the serum from the blood, washing twice with phosphate buffered saline (PBS), and adding phosphate buffered saline to the removed serum portion.

An absorbent article was produced in the same manner as Example 2, except that the tri-C2L oil fatty acid glyceride was coated at a basis weight of about 5 g/m², and the rewetting rate of each of the aforementioned blood samples was evaluated. Measurement was performed 3 times for each blood sample, and the average value was recorded.

The results are shown in Table 3 below.

TABLE 3

| | | | Rewetting rate (%) | |
| No. | Animal species | Type of blood | With blood modifying agent | Without blood modifying agent |
| --- | --- | --- | --- | --- |
| 1 | Human | Defibrinated blood | 1.6 | 5.0 |
| 2 | | Defibrinated serum | 0.2 | 2.6 |
| 3 | | Defibrinated blood cells | 0.2 | 1.8 |
| 4 | | EDTA blood | 2.6 | 10.4 |
| 5 | | EDTA plasma | 0.0 | 5.8 |
| 6 | | EDTA blood cells | 0.2 | 4.3 |
| 7 | Horse | Defibrinated blood | 0.0 | 8.6 |
| 8 | | Defibrinated serum | 0.2 | 4.2 |
| 9 | | Defibrinated blood cells | 0.2 | 1.0 |
| 10 | | EDTA blood | 6.0 | 15.7 |
| 11 | | EDTA plasma | 0.1 | 9.0 |
| 12 | | EDTA blood cells | 0.1 | 1.8 |
| 13 | Sheep | Defibrinated blood | 0.2 | 5.4 |
| 14 | | Defibrinated serum | 0.3 | 1.2 |
| 15 | | Defibrinated blood cells | 0.1 | 1.1 |
| 16 | | EDTA blood | 2.9 | 8.9 |
| 17 | | EDTA plasma | 0.0 | 4.9 |
| 18 | | EDTA blood cells | 0.2 | 1.6 |

The same trend was seen with human and sheep blood as with the horse EDTA blood, as obtained in Example 2. A similar trend was also observed with defibrinated blood and EDTA blood.

Example 3

[Evaluation of Blood Retention]
The blood retention was evaluated for a top sheet comprising a blood modifying agent and a top sheet comprising no blood modifying agent.
[Test Methods]
(1) A tri-C2L oil fatty acid glyceride was atomized on the skin contact surface of a top sheet formed from an air-through nonwoven fabric (composite fiber composed of polyester and polyethylene terephthalate, basis weight: 35 g/m²), using a control seam HMA gun, for coating to a basis weight of about 5 g/m². For comparison, there was also prepared a sheet without coating with the tri-C2L oil fatty acid glyceride. Next, both the tri-C2L oil fatty acid glyceride-coated top sheet and the non-coated top sheet were cut to a size of 0.2 g, and the mass: a (g) of the cell strainer+top sheet was precisely measured.

(2) After adding about 2 mL of horse EDTA blood from the skin contact surface side, it was allowed to stand for 1 minute.

(3) The cell strainer was set in a centrifuge tube, and subjected to spin-down to remove the excess horse EDTA blood.

(4) The mass: b (g) of the top sheet containing the cell strainer+horse EDTA blood was measured.

(5) The initial absorption (g) per 1 g of top sheet was calculated by the following formula.

$$\text{Initial absorption }(g)=[b(g)-a(g)]/0.2(g)$$

(6) The cell strainer was again set in the centrifuge tube and centrifuged at room temperature for 1 minute at approximately 1,200 G.

(7) The mass: c (g) of the top sheet containing the cell strainer+horse EDTA blood was measured.

(8) The post-test absorption (g) per 1 g of top sheet was calculated by the following formula.

$$\text{Post-test absorption}=[c(g)-a(g)]/0.2(g)$$

(9) The blood retention (%) was calculated according to the following formula.

$$\text{Blood retention (mass \%)}=100\times\text{post-test absorption }(g)/\text{initial absorption }(g)$$

The measurement was conducted 3 times, and the average value was recorded.

The results are shown in Table 4 below.

TABLE 4

| | Blood retention (%) | |
|---|---|---|
| | With blood modifying agent | Without blood modifying agent |
| Horse EDTA blood | 3.3 | 9.2 |

The top sheets comprising blood modifying agents had low blood retentions, suggesting that blood rapidly migrated into the absorbent body after absorption.

Example 4

[Viscosity of Blood Containing Blood Modifying Agent]

The viscosity of the blood modifying agent-containing blood was measured using a Rheometric Expansion System ARES (Rheometric Scientific, Inc.). After adding 2 mass % of PANACET 810s to horse defibrinated blood, the mixture was gently agitated to form a sample, the sample was placed on a 50 mm-diameter parallel plate, with a gap of 100 μm, and the viscosity was measured at 37±0.5° C. The sample was not subjected to a uniform shear rate due to the parallel plate, but the average shear rate indicated by the device was $10 \text{ s}^{-1}$.

The viscosity of the horse defibrinated blood containing 2 mass % PANACET 810s was 5.9 mPa·s, while the viscosity of the horse defibrinated blood containing no blood modifying agent was 50.4 mPa·s. Thus, the horse defibrinated blood containing 2 mass % PANACET 810s clearly had an approximately 90% lower viscosity than the blood containing no blood modifying agent.

It is known that blood contains components, such as blood cells and has thixotropy, and it is believed that the blood modifying agent of this disclosure can lower blood viscosity in the low viscosity range. Lowering the blood viscosity presumably allows absorbed menstrual blood to rapidly migrate from the top sheet to the absorbent body.

Example 5

[Photomicrograph of Blood Modifying Agent-Containing Blood]

Menstrual blood was sampled from healthy volunteers onto thin plastic wrap, and PANACET 810s dispersed in a 10-fold mass of phosphate-buffered saline was added to a portion thereof to a PANACET 810s concentration of 1 mass %. The menstrual blood was dropped onto a slide glass, a cover glass was placed thereover, and the state of the erythrocytes was observed with an optical microscope. A photomicrograph of menstrual blood containing no blood modifying agent is shown in FIG. 12(a), and a photomicrograph of menstrual blood containing PANACET 810s is shown in FIG. 12(b).

From FIG. 12 it is seen that the erythrocytes formed aggregates, such as rouleaux in the menstrual blood containing no blood modifying agent, while the erythrocytes were stably dispersed in the menstrual blood containing PANACET 810s. This suggests that the blood modifying agent functions to stabilize erythrocytes in blood.

Example 6

[Surface Tension of Blood Containing Blood Modifying Agent]

The surface tension of blood containing a blood modifying agent was measured by the pendant drop method, using a Drop Master500 contact angle meter by Kyowa Interface Science Co., Ltd. The surface tension was measured after adding a prescribed amount of blood modifying agent to sheep defibrinated blood, and thoroughly shaking.

Figure 13:
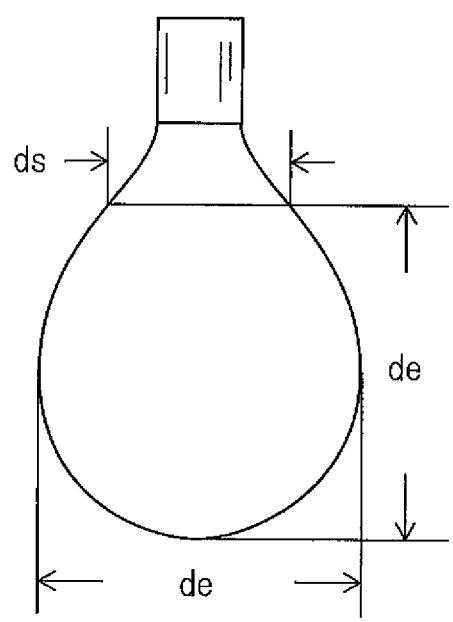
FIG. 13 is a diagram illustrating a method of measuring surface tension.

The measurement was accomplished automatically with a device, and the surface tension γ was determined by the following formula (see FIG. 13).

$$\gamma = g \times \rho \times (de)^2 \times 1/H$$

g: Gravitational constant
1/H: Correction factor determined from ds/de
ρ: Density
de: Maximum diameter
ds: Diameter at location of increase by de from dropping edge The density ρ was measured at the temperatures listed in Table 5, according to JIS K 2249-1995, "Density test methods and density/mass/volume conversion tables", "5. Vibrating density test method".

The measurement was accomplished using a DA-505 by Kyoto Electronics Co., Ltd.

The results are shown in Table 5 below.

TABLE 5

| | Blood modifying agent | | | |
|---|---|---|---|---|
| No. | Type | Amount (mass %) | Measuring temperature (° C.) | Surface tension (mN/m) |
| 1 | — | — | 35 | 62.1 |
| 2 | PANACET | 0.01 | 35 | 61.5 |
| 3 | 810s | 0.05 | 35 | 58.2 |
| 4 | | 0.10 | 35 | 51.2 |
| 5 | ELECTOL WE20 | 0.10 | 35 | 58.8 |
| 6 | PARLEAM 6 | 0.10 | 35 | 57.5 |
| 7 | — | — | 50 | 56.3 |
| 8 | WILBRITE cp9 | 0.10 | 50 | 49.1 |

Table 5 shows that the blood modifying agent can lower the surface tension of blood despite its very low solubility in water, as seen by a water solubility of about 0.00-0.05 g in 100 g of water at 25° C.

Lowering the surface tension of blood presumably allows absorbed blood to rapidly migrate from the top sheet to the absorbent body, without being retained between the top sheet fibers.

REFERENCE SIGNS LIST

1 Sanitary napkin (absorbent article)
2 Top sheet (liquid-permeable sheet)
3 Back sheet (liquid-impermeable sheet)
4 Absorbent body
20 Excreta-receiving region (liquid-receiving region)
21 Extensible region
22 Flexible region
210 Bellows structure

The invention claimed is:

1. An absorbent article, comprising:
a liquid-permeable sheet, a liquid-impermeable sheet and an absorbent body provided between the liquid-permeable sheet and the liquid-impermeable sheet,
wherein
the liquid-permeable sheet has
an extensible region having an extendable bellows structure, and
a flexible region encompassing the extensible region,
the extensible region and the flexible region overlap the absorbent body and are formed in a liquid-receiving region adapted to receive a liquid supplied to the liquid-permeable sheet,
a liquid permeation hole is formed in the extensible region, and no liquid permeation hole is formed in the flexible region,
the extendable bellows structure has mountain and valley folds laid out in a lengthwise direction of the absorbent article and aligned in a widthwise direction of the absorbent article,
the liquid permeation hole is formed in a side section of the extendable bellows structure, said side section connecting an uppermost section of one of the mountain folds and a lowermost section of an adjacent one of the valley folds,
wherein the liquid permeation hole is spaced away from the uppermost section of said one of the mountain folds and the lowermost section of said adjacent one of the valley folds,
wherein the flexible region is in plane with the uppermost section of said one of the mountain folds, and
wherein the liquid permeable sheet comprises a blood modifying agent with an IOB of 0.00-0.60, a melting point of 45° C. or less, and a water solubility of 0.00-0.05 g in 100 g of water at 25° C.

2. The absorbent article according to claim 1, wherein
the liquid-permeable sheet has a plurality of extensible regions in the liquid-receiving region and including said extensible region, each of the extensible regions having an extendable bellows structure, and
the flexible region encompasses each of the extensible regions.

3. The absorbent article according to claim 2, wherein
the flexible region is formed in a net-shaped pattern, and each of the extensible regions is formed inside a mesh unit of the net-shaped pattern.

4. The absorbent article according to claim 3, wherein the flexible region has
roughly linear first regions laid out in a direction crossing a lengthwise direction of the absorbent article and aligned in an approximately parallel manner, and
roughly linear second regions laid out in a direction crossing the first regions and aligned in an approximately parallel manner.

5. The absorbent article according to claim 1, wherein a compressed groove is formed on a perimeter of the liquid-receiving region.

6. The absorbent article according to claim 1, wherein the blood modifying agent is selected from the group consisting of following items (i)-(iii) and combinations thereof:
(i) a hydrocarbon;
(ii) a compound having (ii-1) a hydrocarbon moiety, and (ii-2) one or more, same or different groups selected from the group consisting of carbonyl group (—CO—) and oxy group (—O—) inserted between a C—C single bond of the hydrocarbon moiety; and
(iii) a compound having (iii-1) a hydrocarbon moiety, (iii-2) one or more, same or different groups selected from the group consisting of carbonyl group (—CO—) and oxy group (—O—) inserted between a C—C single bond of the hydrocarbon moiety, and (iii-3) one or more, same or different groups selected from the group consisting of carboxyl group (—COOH) and hydroxyl group (—OH) substituted for a hydrogen of the hydrocarbon moiety;
with the proviso that when 2 or more oxy groups are inserted in the compound of (ii) or (iii), the oxy groups are not adjacent.

7. The absorbent article according to claim 1, wherein the blood modifying agent is selected from the group consisting of following items (i')-(iii') and combinations thereof:
(i') a hydrocarbon;
(ii') a compound having (ii'-1) a hydrocarbon moiety, and (ii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety; and
(iii') a compound having (iii'-1) a hydrocarbon moiety, (iii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety, and (iii'-3) one or more, same or different groups selected from the group consisting of carboxyl group (—COOH) and hydroxyl group (—OH) substituted for a hydrogen on the hydrocarbon moiety;
with the proviso that when 2 or more same or different bonds are inserted in a compound of (ii') or (iii'), the bonds are not adjacent.

8. The absorbent article according to claim 1, wherein the blood modifying agent is selected from the group consisting of following items (A)-(F) and combinations thereof:
(A) an ester of (A1) a compound having a chain hydrocarbon moiety and 2-4 hydroxyl groups substituted for hydrogens on the chain hydrocarbon moiety, and (A2) a compound having a chain hydrocarbon moiety and 1 carboxyl group substituted for a hydrogen on the chain hydrocarbon moiety;
(B) an ether of (B1) a compound having a chain hydrocarbon moiety and 2-4 hydroxyl groups substituted for hydrogens on the chain hydrocarbon moiety, and (B2) a compound having a chain hydrocarbon moiety and 1 hydroxyl group substituted for a hydrogen on the chain hydrocarbon moiety;
(C) an ester of (C1) a carboxylic acid, hydroxy acid, alkoxy acid or oxoacid comprising a chain hydrocarbon moiety and 2-4 carboxyl groups substituted for hydrogens on the chain hydrocarbon moiety, and (C2) a compound having a chain hydrocarbon moiety and 1 hydroxyl group substituted for a hydrogen on the chain hydrocarbon moiety;
(D) a compound having a chain hydrocarbon moiety and one bond selected from the group consisting of ether bonds (—O—), carbonyl bonds (—CO—), ester bonds (—COO—) and carbonate bonds (—OCOO—) inserted between a C—C single bond of the chain hydrocarbon moiety;
(E) a polyoxy $C_2$-$C_6$ alkylene glycol, or its ester or ether; and
(F) a chain hydrocarbon.

9. The absorbent article according to claim 1, wherein the blood modifying agent is selected from the group consisting of ($a_1$) an ester of a chain hydrocarbon tetraol and at least one fatty acid, ($a_2$) an ester of a chain hydrocarbon triol and at least one fatty acid, ($a_3$) an ester of a chain hydrocarbon diol and at least one fatty acid, ($b_1$) an ether of a chain hydrocarbon tetraol and at least one aliphatic monohydric alcohol, ($b_2$) an ether of a chain hydrocarbon triol and at least one aliphatic monohydric alcohol, ($b_3$) an ether of a chain hydrocarbon diol and at least one aliphatic monohydric alcohol, ($c_1$) an ester of a chain hydrocarbon tetracarboxylic acid, hydroxy acid, alkoxy acid or oxoacid with 4 carboxyl groups, and at least one aliphatic monohydric alcohol, ($c_2$) an ester of a chain hydrocarbon tricarboxylic acid, hydroxy acid, alkoxy acid or oxoacid with 3 carboxyl groups, and at least one aliphatic monohydric alcohol, ($c_3$) an ester of a chain hydrocarbon dicarboxylic acid, hydroxy acid, alkoxy acid or oxoacid with 2 carboxyl groups, and at least one aliphatic monohydric alcohol, ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, ($d_4$) a dialkyl carbonate, ($e_1$) a polyoxy $C_2$-$C_6$ alkylene glycol, ($e_2$) an ester of a polyoxy $C_2$-$C_6$ alkylene glycols and at least one fatty acid, ($e_3$) an ether of a polyoxy $C_2$-$C_6$ alkylene glycol and at least one aliphatic monohydric alcohol, ($e_4$) an ester of a polyoxy $C_2$-$C_6$ alkylene glycols and a chain hydrocarbon tetracarboxylic acid, chain hydrocarbon tricarboxylic acid or chain hydrocarbon dicarboxylic acid, ($e_5$) an ether of a polyoxy $C_2$-$C_6$ alkylene glycol and a chain hydrocarbon tetraol, chain hydrocarbon triol or chain hydrocarbon diol, and ($f_1$) a chain alkane, and combinations thereof.

10. The absorbent article according to claim 1, wherein an open area of the liquid permeation hole is in a range of 0.001 to 1 $mm^2$.

* * * * *